United States Patent [19]

Torii et al.

[11] Patent Number: 4,603,014

[45] Date of Patent: Jul. 29, 1986

[54] THIAZOLINOAZETIDINONE DERIVATIVES AND PROCESS FOR THE PREPARATION OF THE SAME

[75] Inventors: Sigeru Torii; Hideo Tanaka; Junzo Nokami; Michio Sasaoka; Norio Saito; Takashi Shiroi, all of Okayama; Akira Tanaka, Naruto, all of Japan

[73] Assignee: Otsuka Kagaku Yakuhin Kabushiki Kaisha, Japan

[21] Appl. No.: 625,621

[22] Filed: Jun. 28, 1984

Related U.S. Application Data

[62] Division of Ser. No. 370,034, Apr. 20, 1982, Pat. No. 4,482,491.

[30] Foreign Application Priority Data

May 1, 1981 [JP] Japan .................................. 56-67135
May 1, 1981 [JP] Japan .................................. 56-67136
May 8, 1981 [JP] Japan .................................. 56-69687
Nov. 17, 1981 [JP] Japan .................................. 56-184877

[51] Int. Cl.$^4$ .................. C07D 205/08; C07D 513/04; C25C 3/36; C25B 3/06
[52] U.S. Cl. .................................. 260/245.4; 204/81; 204/157.98; 544/17; 544/18

[58] Field of Search ........ 260/245.4; 204/81, 158 HA

[56] References Cited

U.S. PATENT DOCUMENTS 4,271,285 6/1981 Tsuji ................................. 260/245.4

Primary Examiner—Mark L. Berch
Attorney, Agent, or Firm—Larson and Taylor

[57] ABSTRACT

This invention provides thiazolinoazetidinone derivatives represented by the formula

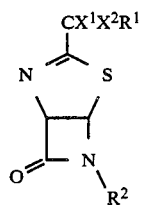

and processes for preparing the same. The thiazolinoazetidinone derivatives are used as the intermediates for producing cephalosporin compounds useful as antibiotic agents.

33 Claims, No Drawings

THIAZOLINOAZETIDINONE DERIVATIVES AND PROCESS FOR THE PREPARATION OF THE SAME

This is a division of application Ser. No. 370,034 filed Apr. 20, 1982, now U.S. Pat. No. 4,482,491.

This invention relates to novel thiazolinoazetidinone derivatives and a process for preparing the same, and more particularly to thiazolinoazetidinone derivatives represented by the formula

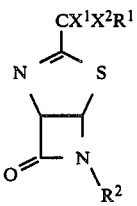

wherein $X^1$ and $X^2$ each represent a hydrogen atom or a halogen atom; $R^1$ represents an aryl or an aryloxy; $R^2$ represents

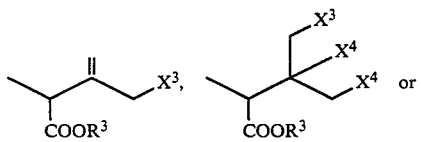

or

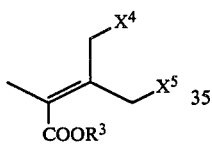

wherein $R^3$ represents a lower alkyl substituted with at least one aryl group, a lower alkyl substituted with at least one aryloxy group or a lower alkyl optionally substituted with at least one halogen atom, $X^3$ and $X^4$, which are the same or different, each represent a halogen atom, and $X^5$ represents $X^3$ or $X^4$.

The present invention provides novel intermediates for the preparation of cephalosporin compounds which are useful as antibiotics.

The invention provides also processes for preparing the novel intermediates.

The invention further provides a novel process for preparing cephalosporin compounds from the foregoing intermediates.

Other features of the invention will be made apparent by the following description.

Examples of the aryl groups represented by $R^1$ in the formula (I) are phenyl, tolyl, xylyl, naphthyl, p-chlorophenyl, p-methoxyphenyl, p-nitrophenyl, p-hydroxyphenyl, etc. Examples of the aryloxy groups represented by $R^1$ are phenoxy, tolyloxy, xylyloxy, naphthyloxy, p-chlorophenyloxy, p-methoxyphenyloxy, p-nitrophenyloxy, p-hydroxyphenyloxy, etc.

Examples of the lower alkyl groups substituted with at least one aryl group and represented by $R^3$ are benzyl, p-nitrobenzyl, diphenylmethyl, 2-phenylethyl, 2-(p-nitrophenyl)ethyl, 3-phenylpropyl, 3-(p-nitrophenyl)propyl, 3-(p-nitrophenyl)propyl, etc. Examples of the lower alkyl groups substituted with aryloxy and represented by $R^3$ are phenoxymethyl, p-nitrophenoxymethyl, 2-phenoxyethyl, 2-(p-nitrophenoxy)ethyl, 3-phenoxypropyl, 3-(p-nitrophenoxy)propyl, etc. Examples of the lower alkyl groups represented by $R^3$ and optionally substituted with at least one halogen atom are methyl, ethyl, n-propyl, isopropyl, n-butyl, tert-butyl, 2-chloroethyl, 2,2,2-trichloroethyl, etc.

The halogen atoms represented by $X^1$, $X^2$, $X^3$, $X^4$ and $X^5$ include a chlorine atom, a bromine atom, an iodine atom, etc.

The thiazolinoazetidinone derivatives having the formula (I) (hereinafter referred to as compounds) (I) include three classes of compounds represented by the following formulae (Ia), (Ib) and (Ic), respectively. (These compounds are hereinafter referred to as compounds (Ia), (Ib) and (Ic), respectively.)

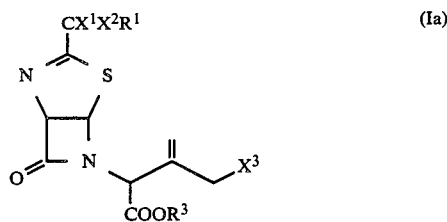

wherein $R^1$, $R^3$, $X^1$, $X^2$ and $X^3$ are as defined above.

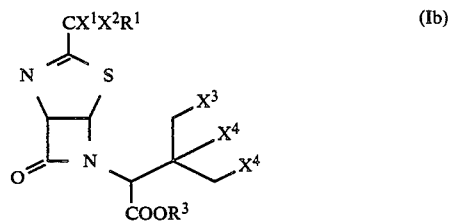

wherein $R^1$, $R^3$, $X^1$, $X^2$, $X^3$ and $X^4$ are as defined above.

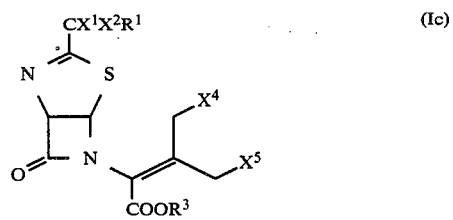

wherein $R^1$, $R^3$, $X^1$, $X^2$, $X^4$ and $X^5$ are as defined above.

Table I below shows specific examples of compounds (Ia).

TABLE I

| $R^1$ | $R^3$ | $X^1$ | $X^2$ | $X^3$ |
|---|---|---|---|---|
| phenyl | CH₃— | H | H | Cl |
| " | Cl₃CCH₂— | " | " | " |
| " | (CH₃)₃C— | " | " | " |
| " | benzyl | " | " | " |

TABLE I-continued

| R¹ | R³ | X¹ | X² | X³ |
|----|----|----|----|----|
| " | O₂N-C₆H₄-CH₂- | " | " | " |
| " | (C₆H₅)₂CH- | " | " | " |
| " | C₆H₅-O-CH₂- | " | " | " |
| C₆H₅-O- | CH₃- | " | " | " |
| " | Cl₃CCH₂- | " | " | " |
| " | (CH₃)₃C- | " | " | " |
| " | C₆H₅-CH₂- | " | " | " |
| " | O₂N-C₆H₄-CH₂- | " | " | " |
| " | (C₆H₅)₂CH- | " | " | " |
| " | C₆H₅-O-CH₂- | " | " | " |
| C₆H₅- | CH₃- | Cl | Cl | " |
| " | Cl₃CCH₂- | " | " | " |
| " | (CH₃)₃C- | " | " | " |
| " | C₆H₅-CH₂- | " | " | " |
| " | O₂N-C₆H₄-CH₂- | " | " | " |
| " | (C₆H₅)₂CH- | " | " | " |
| " | C₆H₅-O-CH₂- | " | " | " |
| C₆H₅-O- | CH₃- | " | " | " |
| " | Cl₃CCH₂- | " | " | " |
| " | (CH₃)₃C- | " | " | " |
| " | C₆H₅-CH₂- | " | " | " |
| " | O₂N-C₆H₄-CH₂- | " | " | " |
| " | (C₆H₅)₂CH- | " | " | " |
| " | C₆H₅-O-CH₂- | " | " | " |

Table II below shows specific examples of compounds (Ib).

TABLE II

| R¹ | R³ | X¹ | X² | X³ | X⁴ |
|----|----|----|----|----|----|
| C₆H₅- | CH₃- | H | H | Cl | Cl |
| " | Cl₃CCH₂- | " | " | " | " |
| " | (CH₃)₃C- | " | " | " | " |

TABLE II-continued

| R¹ | R³ | X¹ | X² | X³ | X⁴ |
|---|---|---|---|---|---|
| " | PhCH₂— | " | " | " | " |
| " | 4-O₂N-C₆H₄-CH₂— | " | " | " | " |
| " | Ph₂CH— | " | " | " | " |
| " | PhO-CH₂— | " | " | " | " |
| PhO— | CH₃— | | | | |
| " | Cl₃CCH₂— | " | " | " | " |
| " | (CH₃)₃C— | " | " | " | " |
| " | PhCH₂— | " | " | " | " |
| " | 4-O₂N-C₆H₄-CH₂— | " | " | " | " |
| " | Ph₂CH— | " | " | " | " |
| " | PhO-CH₂— | " | " | " | " |
| Ph— | CH₃— | Cl | Cl | " | " |
| " | Cl₃CCH₂— | " | " | " | " |
| " | (CH₃)₃C— | " | " | " | " |
| " | PhCH₂— | " | " | " | " |

TABLE II-continued

| R¹ | R³ | X¹ | X² | X³ | X⁴ |
|---|---|---|---|---|---|
| " | 4-O₂N-C₆H₄-CH₂— | " | " | " | " |
| " | Ph₂CH— | " | " | " | " |
| " | PhO-CH₂— | " | " | " | " |
| PhO— | CH₃— | " | " | " | " |
| " | Cl₃CCH₂— | " | " | " | " |
| " | (CH₃)₃C— | " | " | " | " |
| " | PhCH₂— | " | " | " | " |
| " | 4-O₂N-C₆H₄-CH₂— | " | " | " | " |
| " | Ph₂CH— | " | " | " | " |
| " | PhO-CH₂— | " | " | " | " |

Table III below shows specific examples of compounds (Ic).

TABLE III

| R¹ | R³ | X¹ | X² | X⁴ | X⁵ |
|---|---|---|---|---|---|
| Ph— | CH₃— | H | H | Cl | Cl |
| " | Cl₃CCH₂— | " | " | " | " |
| " | (CH₃)₃C— | " | " | " | " |

TABLE III-continued

| R¹ | R³ | X¹ | X² | X⁴ | X⁵ |
|---|---|---|---|---|---|
| " | C₆H₅-CH₂- | " | " | " | " |
| " | O₂N-C₆H₄-CH₂- | " | " | " | " |
| " | (C₆H₅)₂CH- | " | " | " | " |
| " | C₆H₅-O-CH₂- | " | " | " | " |
| C₆H₅-O- | CH₃- | " | " | " | " |
| " | Cl₃CCH₂- | " | " | " | " |
| " | (CH₃)₃C- | " | " | " | " |
| " | C₆H₅-CH₂- | " | " | " | " |
| " | O₂N-C₆H₄-CH₂- | " | " | " | " |
| " | (C₆H₅)₂CH- | " | " | " | " |
| " | C₆H₅-O-CH₂- | " | " | " | " |
| C₆H₅- | CH₃- | Cl | Cl | " | " |
| " | Cl₃CCH₂- | " | " | " | " |
| " | (CH₃)₃C- | " | " | " | " |
| " | C₆H₅-CH₂- | " | " | " | " |
| " | O₂N-C₆H₄-CH₂- | " | " | " | " |
| " | (C₆H₅)₂CH- | " | " | " | " |
| " | C₆H₅-O-CH₂- | " | " | " | " |
| C₆H₅-O- | CH₃- | " | " | " | " |
| " | Cl₃CCH₂- | " | " | " | " |
| " | (CH₃)₃C- | " | " | " | " |
| " | C₆H₅-CH₂- | " | " | " | " |
| " | O₂N-C₆H₄-CH₂- | " | " | " | " |
| " | (C₆H₅)₂CH- | " | " | " | " |
| " | C₆H₅-O-CH₂- | " | " | " | " |

The compounds (Ia), (Ib) and (Ic) are all novel compounds heretofore undisclosed in literature.

The thiazolinoazetidinone derivatives of the formula (I) can be prepared by various processes. Exemplary of the process are hereinafter stated.

For example, the compound (Ia) wherein X¹ and X² are a halogen atom can be produced by electrolyzing a known compound represented by the formula

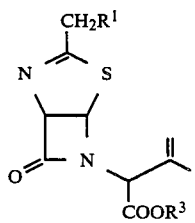 (IV)

wherein $R^1$ and $R^3$ are as defined above in the presence of halides [The latter compound is hereinafter referred to as compound (IV)].

Useful halides include a wide variety of known hydrohalogenic acids such as hydrochloric acid, hydrobromic acid, hydroiodic acid, among which the hydrochloric acid is preferred. Also, usable as the halide are various conventional compounds such as ammonium chloride, tetramethylammonium chloride, tetraethylammonium chloride, benzyltrimethylammonium chloride and like quaternary ammonium salts, lithium chloride, sodium chloride, potassium chloride and like alkali metal salts, magnesium chloride, barium chloride, calcium chloride and like salts of alkaline earth metals and other chlorides; ammonium bromide, tetramethylammonium bromide, tetraethylammonium bromide, benzyltrimethylammonium bromide and like quaternary ammonium salts, sodium bromide, cerium bromide, lithium bromide and like alkali metal salts, magnesium bromide and like salts of alkaline earth metals and other bromides; ammonium iodide, tetramethylammonium iodide, tetraethylammonium iodide and like quaternary ammonium salts, lithium iodide, potassium iodide, sodium iodide and like alkali metal salts and other iodides, etc. The amount of the hydrohalogenic acid and/or halide to be used is not particularly limited but widely variable. They are used in an amount of about 0.5 to about 10 moles, preferably about 1 to about 8 moles, per mole of the compound (IV). The halide is effective when used in conjunction with mineral acid or organic acid. Examples of useful mineral acids are sulfuric acid, sodium hydrogensulfate, potassium hydrogensulfate, phosphoric acid, boric acid, etc. Useful organic acids include formic acid, acetic acid, propionic acid, butyric acid, oxalic acid, citric acid and like carboxylic acid; p-toluenesulfonic acid, methanesulfonic acid and like sulfonic acids, etc. It is preferred to use the mineral acid or organic acid in an amount of about 0.5 to about 10 moles, preferably about 1 to about 8 moles, per mole of the compound (IV). Generally used as the reaction medium is a mixture of water and organic solvent. Usable as the organic solvent are various solvents inert to halogenation such as methyl formate, ethyl formate, methyl acetate, ethyl acetate, butyl acetate, ethyl propionate and like esters; dichloromethane, chloroform, carbon tetrachloride, dichloroethane, dibromoethane, chlorobenzene and like halogenated hydrocarbons; diethyl ether, dibutyl ether, dioxane, tetrahydrofuran and like ethers; acetonitrile, butyronitrile and like nitriles; pentane, hexane, cyclohexane and like hydrocarbons; carbon disulfide, etc.

The electrolysis can be performed at either controlled potential or constant current. The cathode current density is usually in the range of about 1 to about 500 mA/cm$^2$, preferably about 5 to about 200 mA/cm$^2$. The required electric charge is usually about 2 to about 50 F, preferably about 3 to about 40 F, per mole of the starting material, although variable depending on the concentration of the substrate, the kind of the solvent, the type or shape of the electrolytic bath, etc. Useful electrodes include those usually used, such as those of platinum, carbon, stainless steel, titanium, nickel or the like. The reaction temperature is not particularly limited as far as it is below a level at which there occurs the decomposition or conversion of the starting material and reaction product. It is usually about −30° to about 60° C., preferably about −20° to about 30° C. The electrolytic bath is used with or without a diaphragm. Thus the compounds (Ia) wherein $X^1$ and $X^2$ are halogen atoms are prepared.

The compounds (Ia) wherein $X^1$ and $X^2$ are hydrogen atoms can be prepared for example by permitting zinc to act on the compound (Ia) prepared above wherein $X^1$ and $X^2$ are halogen atoms in the presence of lower fatty acid.

Useful lower fatty acids include formic acid, acetic acid, propionic acid, butyric acid, valeric acid, etc. The amount of the lower fatty acid to be used is not particularly limitative but is determined over a wide range. It is usually used in an amount of about 1 to about 10 moles, preferably about 2 to about 4 moles, per mole of the starting compound. The amount of the zinc to be used is not limited within a particular range but is widely variable. It is usually employed in an amount of about 1 to about 10 moles, particularly about 2 to about 4 moles, per mole of the starting compound. The foregoing reaction is carried out usually in an organic solvent. Usable as the organic solvent are various solvents inert to the starting compound and the end product, such as ethyl acetate, methyl acetate, methyl propionate and like esters; diethyl ether, tetrahydrofuran, dioxane and like ethers; methylene chloride, dichloroethane, chloroform, carbon tetrachloride and like halogenated hydrocarbon; benzene, toluene, xylene and like aromatic hydrocarbons, etc. It is preferred to carry out the foregoing reaction at a relatively low temperature ranging preferably from about −50° to about 30° C. Thus the compounds (Ia) wherein $X^1$ and $X^2$ are hydrogen atoms are prepared.

The compounds (Ia) wherein $X^1$, $X^2$ and $X^3$ represent different halogen atoms can be prepared for example from the compound (Ia) prepared above wherein $X^1$ and $X^2$ are halogen atoms by replacing the halogen atoms represented by $X^1$ and $X^2$ with other halogen atoms. Stated more specifically the compound (Ia) wherein $X^1$, $X^2$ and $X^3$ are chlorine atoms can be converted into compound (Ia) wherein $X^1$ and $X^2$ are iodine atoms and $X^3$ is a chlorine atom. This reaction is carried out by allowing alkali metal iodide to act on the compound (Ia) in a ketone solvent. Suitable examples of useful ketone solvents are acetone, methyl ethyl ketone and like lower ketones among which the acetone is more suitable. Preferred alkali metal iodides useful as the reaction reagent include sodium iodide, potassium iodide, etc. This reagent is usually used in an amount of more than 1 mole, preferably about 1 to about 2 moles, per mole of the compound (Ia). It is favorable to conduct the reaction for 30 minutes to 5 hours at a temperature between room temperature and the temperature at which the solvent is refluxed.

The compounds (Ib) can be prepared by mixing together the compound (Ia), halogen and a suitable organic solvent and reacting the compound (Ia) with the halogen while radiating the mixture with light.

Useful halogens include, for example, chlorine, bromine, iodine, etc. These halogens are usually used in the form of a diatomic molecule. Usable as the organic solvent are those inert to the halogen such as dichloromethane, dibromoethane, dichloroethane, chloroform, carbon tetrachloride and like halogenated hydrocarbons; methyl acetate, ethyl acetate, methyl formate, butyl acetate, ethyl propionate and like esters; diethyl ether, dibutyl ether, tetrahydrofuran, dioxane and like ethers; acetonitrile, butyronitrile and like nitriles; pentane, hexane, cyclohexane and like hydrocarbons; benzene, toluene, xylene, chlorobenzene and like aromatic hydrocarbons; carbon disulfide; or mixtures of these solvents, etc. The amount of the halogen relative to the compound (Ia), although nonlimitative and widely variable, is usually about 0.5 to about 10 moles, preferably about 1 to about 5 moles, per mole of the latter. With this invention, it is essential that the compound (Ia) be reacted with halogen while being irradiated with light. Without the light irradiation, the reaction may proceed to some extent, but gives the compound (Ib) in extremely low yields and produces large amount of by-products. Even when the reaction mixture is irradiated with sunlight, the reaction affords the compound (Ib) in relatively low and markedly irregular yields, hence undesirable. Useful as the source of light is a tungusten lamp or the like which is usually employed in a photochemical reaction. The suitable reaction temperature is in the range of about −50° to about 30° C.

Alternatively, the compounds (Ib) can be prepared by electrolyzing the compound (Ia) in the presence of hydrohalogenic acid and/or halide while irradiating the mixture with light.

The light sources employed in the reaction between the compound (Ia) and the halogen are usable in the foregoing electrolysis of the compound (Ia). Usable as the hydrohalogenic acid and halide are those which are used in the electrolysis of the compound (IV). The amount of the hydrohalogenic acid and/or halide is not particularly limited but suitably determined over a wide range. It is usually about 0.5 to about 10 moles, preferably about 1 to about 5 moles, per mole of the compound (Ia). This reaction proceeds effectively when a mineral acid or organic acid is present in the reaction system. Examples of useful mineral acids and organic acids include those which can be used for the electrolysis of the compound (IV).

The electrolysis can be performed at either controlled potential or constant current. The cathode current density is usually in the range of about 1 to about 500 mA/cm$^2$, preferably about 5 to about 100 mA/cm$^2$. The required electric charge is usually about 2 to about 70 F, per mole of the starting material, although variable depending on the concentration of the substrate, the kind of the solvent, the type or shape of the electrolytic bath, etc. Useful electrodes include those usually used, such as those of platinum, carbon, stainless steel, titanium, nickel or the like. The reaction temperature is not particularly limited as far as it is below a level at which there occurs the decomposition or conversion of the starting material and reaction product. It is usually about −30° to about 60° C., preferably about −20° to about 30° C. The electrolytic bath is used with or without a diaphragm. Thus compounds (Ib) can be produced.

The compounds (Ib) wherein $X^1$ and $X^2$ are hydrogen atoms can also be prepared by permitting zinc to act on the compound (Ib) wherein $X^1$ and $X^2$ are halogen atoms in the presence of lower fatty acid. This reaction can be carried out under the same reaction conditions as those employed for preparing the compound (Ia) wherein $X^1$ and $X^2$ are hydrogen atoms under which one permits zinc to act on the compound (Ia) wherein $X^1$ and $X^2$ are halogen atoms in the presence of lower fatty acid.

The compounds (Ic) can be prepared by bringing a base compound into contact with the compound (Ib) obtained above.

Examples of useful bases include those heretofore known such as dimethylamine, diethylamine, triethylamine, ethyldiisopropylamine, piperidine, lutidine, pyridine, 1,5-diazabicyclo[5,4,0]undecene-5,1,5-diazabicyclo[4,3,0]nonene-5 and like organic amines. The amount of the base to be used is not particularly limited and suitably determined over a wide range. It is usually about 0.5 to about 10 moles, preferably about 1 to about 5 moles, per mole the compound of the formula (Ib). The foregoing reaction may be effected either in an organic solvent or in the above-mentioned base which acts as a solvent as well. Usable as the organic solvent are various solvents inert to the starting compound and end product, such as methylene chloride, chloroform, carbon tetrachloride, dichloroethane, dibromoethane and like halogenated hydrocarbons; diethyl ether, dibutyl ether, tetrahydrofuran, dioxane and like ethers; pentane, hexane, heptane, octane and like hydrocarbons; benzene, chlorobenzene, toluene, xylene and like aromatic hydrocarbons, etc. The foregoing reaction, although feasible whether at room temperature or increased temperature or with cooling, is usually carried out at a temperature of about −30° to about 80° C., preferably at about 20° and about 60° C. Thus the compounds (Ic) can be prepared.

The compounds (Ic) wherein $X^1$ and $X^2$ are hydrogen atoms can be prepared also by permitting zinc to act on the compound (Ic) wherein $X^1$ and $X^2$ are halogen atoms in the presence of lower fatty acid. This reaction can be conducted under the same conditions as those employed for preparing the compounds (Ia) wherein $X^1$ and $X^2$ are hydrogen atoms under which one allows zinc to act on the compound (Ia) wherein $X^1$ and $X^2$ are halogen atoms in the presence of lower fatty acid.

The compound of the present invention obtained by the foregoing processes can be easily separated from the reaction mixture and purified by the usual means such as solvent extraction, column chromatography, etc.

The aforesaid processes of this invention give end products in high yields under moderate conditions by simplified procedures. Furthermore the separation and purification of end products are easily conducted and do not pose the problem arising from disposal of by-products. Therefore, the present processes are extremely advantageous from commercial viewpoints.

The compounds (I) of this invention are useful as intermediates for synthesizing penicillin and cephalosporin antibiotics.

For example, cephalosporin compounds (VII) useful as antimicrobial agent can be prepared from the compounds (Ia) wherein $X^1$ and $X^2$ are hydrogen atoms by the reaction schematically illustrated below. The compounds (Ia) wherein $X^1$ and $X^2$ are halogen atoms are useful as the intermediates for synthesizing the compounds (Ia) wherein $X^1$ and $X^2$ are hydrogen atoms.

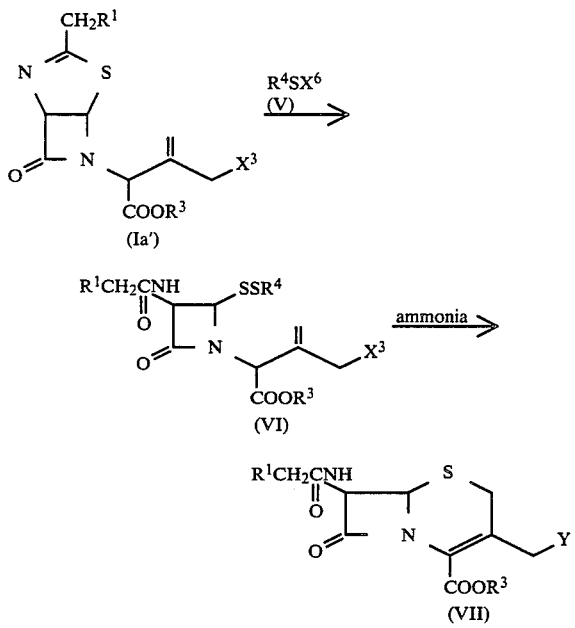

wherein $R^1$, $R^3$ and $X^3$ are as defined above; $R^4$ represents aryl or aromatic heterocyclic group each optionally substituted; $X^6$ is a halogen atom; and Y is a halogen atom or $-SR^4$ (wherein $R^4$ is as defined above).

The reaction between the compounds of the formulae (Ia') and (V) (hereinafter referred to as compounds (Ia') and (V), respectively) is usually effected in a water-containing solvent. Useful water-containing solvents include water-containing dimethyl sulfoxide, water-containing dioxane, etc. Although the amount of the solvent relative to water is not particularly limited, the solvent is used at least in an amount such that the compounds (Ia') and (V) are soluble in the water-containing solvent. The water content in the water-containing solvent is not particularly limited but widely variable. It is usually about 1 to about 500 times, preferably about 10 to about 100 times, the weight of the compound (Ia'). The amount of the compound (V) used relative to the compound (Ia') is not particularly limitative but suitably determined over a wide range. The compound (V) is used in an amount of usually about 1 to about 10 moles, preferably about 1 to about 4 moles, per mole of the compound (Ia'). The reaction is conducted usually at a temperature of about $-10°$ to about $60°$ C., preferably at or in the vicinity of room temperature. The compound (V) to be used in the foregoing reaction is prepared by reacting the corresponding disulfide with an equimolar amount of halogen in carbon tetrachloride or like inert solvent. Either the compound of the formula (V) thus obtained and isolated from the reaction mixture or the reaction mixture itself may be used in the reaction.

The organic solvents to be used in the reaction between the compound (VI) and ammonia include a wide variety of inert solvents. Preferably useful solvents are dimethylformamide, dimethylacetamide or like nonprotonic solar solvents among which the dimethylformamide is espicially preferred. The amount of the compound (VI) relative to ammonia is not particularly limited but suitably determined over a wide range. Usually the ammonia is used in an amount of about 1 to about 3 moles, preferably about 1.5 moles, per mole of the compound (VI). Generally the reaction proceeds favorably at a temperature of about $-78°$ to about $20°$ C., preferably about $-40°$ to about $5°$ C.

Cephalosporin compounds (VII) prepared as above may be either those in which Y is $-SR^4$ or those in which Y is halogen, depending on the type of the group represented by $R^4$. A compound (VII) wherein Y is $-SR^4$ is obtained by using the compound (VI) wherein $R^4$ is pentachlorophenyl, 2-benzothiazolyl, 1,3,4-thiadiazol-5-yl or substituted 1,3,4-thiadiazol-5-yl, or 1,2,3,4-tetrazol-5-yl or substituted 1,2,3,4-tetrazol-5-yl. Upon cyclization of the compound (VI) to the compound (VII), it is possible to introduce into the 3'-position a mercaptothiadiazole group or mercaptotetrazole group which is frequently used as the pendant for cephalosporin antibiotics. Cephalosporin compounds (VII) wherein Y is halogen are suitably used as intermediates for preparing compounds in which various substituents can be introduced by the usual replacement reaction.

Cephalosporin compounds (VIII), (IX) and (X) given below which are useful as antimicrobials can be prepared from the compound (I) wherein $X^1$ and $X^2$ are hydrogen atoms, namely the compound (I').

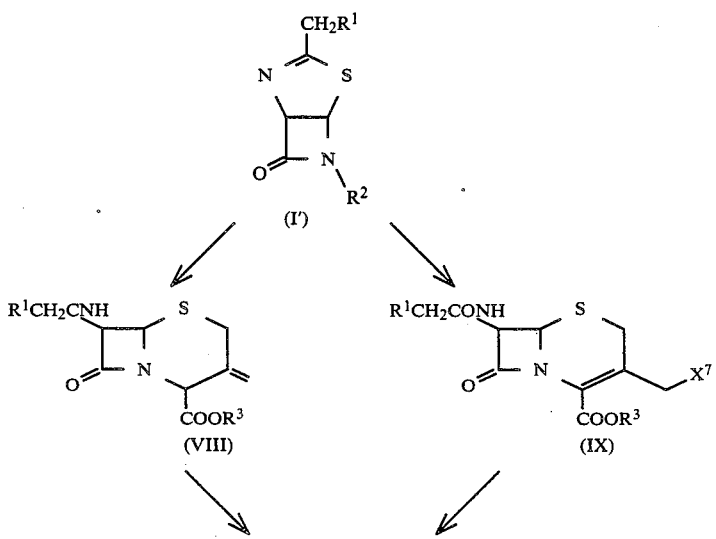

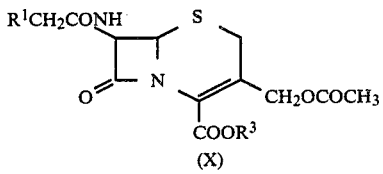

(X)

In the foregoing equation, $R^1$, $R^2$ and $R^3$ are as defined above, and $X^7$ is a halogen atom.

After the completion of the reaction, the cephalosporin compound prepared by the process of this invention can be extracted for separation in the usual manner and then purified by recrystallization or column chromatography.

The processes of this invention afford high yield of cephalosporin compounds with high purity by simplified procedure.

For a better understanding of this invention, examples will be given below.

EXAMPLE 1

A 1 g quantity of sodium chloride was dissolved in 3 ml of water. To the solution were added 0.07 ml of concentrated sulfuric acid, 5 ml of methylene chloride and 50 mg of the compound (IV) wherein $R^1$ is phenyl (hereinafter referred to as Ph) and $R^3$ is $CH_3$ to obtain an electrolyte. Using platinum electrodes (3 cm$^2$), electrolysis was continued at a constant current of 30 mA, 1.6 to 1.8 V and a temperature of 25° C. for about 2 hours. Thereafter, the resulting reaction mixture was extracted with 30 ml of methylene chloride. The extract was washed successively with respective aqueous solutions of sodium sulfite, sodium hydrogencarbonate and sodium chloride, and was dried over anhydrous sodium sulfate. The solvent was distilled off at reduced pressure, affording 74 mg of light yellow liquid. The liquid was subjected to silica gel column chromatography using a 5:1 benzene-ethyl acetate mixture as a developer, giving 62.5 mg of a compound (Ia) wherein $R^1$ is Ph, $R^3$ is $CH_3$, and $X^1$, $X^2$ and $X^3$ are Cl in 96% yield.

IR (cm$^{-1}$) 1780, 1745.

NMR (CDCl$_3$, δ, ppm) 3.75 (s, 3H), 3.81 (s, 2H), 5.14 (s, 2H), 5.41 (s, 1H), 6.05 (s, 2H), 7.3–7.9 (m, 5H).

EXAMPLE 2

There were mixed together 300 mg of a compound (Ia) wherein $R^1$ is Ph, $R^3$ is $CH_3$, and $X^1$, $X^2$, $X^3$ are Cl, 100 mg of zinc powder and 2 ml of methylene chloride. The mixture was cooled to 0° to −5° C. Thereto was added 0.5 ml of acetic acid and the resulting mixture was stirred for 30 minutes. Thereafter, 15 ml of ether was added to the reaction mixture with cooling. Then the organic phase was separated, washed successively with water, an aqueous solution of sodium hydrogencarbonate and a saturated aqueous solution of sodium chloride and dried over anhydrous sodium sulfate. The solvent was distilled off at reduced pressure. The residue was purified by silica gel column chromatography using a 10:1 benzene-ethyl acetate mixture as a developer, giving a compound (Ia) wherein $R^1$ is Ph, $R^3$ is $CH_3$, $X^1$ and $X^2$ are H, and $X^3$ is Cl. Yield 94.5%.

IR (CHCl$_3$, cm$^{-1}$) 1774, 1744.

NMR (CDCl$_3$, δ, ppm) 3.71 (s, 3H), 3.78 (s, 2H), 3.83 (s, 2H), 5.09 (s, 2H), 5.37 (s, 1H), 5.88 (m, 2H), 7.22 (s, 5H).

EXAMPLE 3

There were mixed together 50 mg of a compound (Ia) wherein $R^1$ is Ph, $R^3$ is PhCH$_2$, and $X^1$, $X^2$ and $X^3$ are Cl, 14 mg of zinc powder and 0.7 ml of methylene chloride. The mixture was cooled to 0° to −5° C. Therefore was added 0.2 ml of acetic acid and the resulting mixture was stirred for 30 minutes. The same subsequent procedure as in Example 2 was repeated giving a compound (Ia) wherein $R^1$ is Ph, $R^3$ is PhCH$_2$, $X^1$ and $X^2$ are H and $X^3$ is Cl. Yield 92.5%.

IR (CHCl$_3$, cm$^{-1}$) 1775, 1737.

NMR (CDCl$_3$, δ, ppm) 3.75 (s, 2H), 3.85 (s, 2H), 4.95, 5.10, 5.25 (all s, 1H, total 3H), 5.10 (s, 2H), 5.95 (m, 2H), 7.25 (bs, 10H).

EXAMPLE 4

In 0.5 ml of methylene chloride was dissolved 50 mg of a compound (Ia) wherein $R^1$ is Ph, $R^3$ is $CH_3$ and $X^1$, $X^2$ and $X^3$ are Cl. To the solution was added 1.5 ml of methylene chloride having dissolved therein saturated chlorine. The mixture was irradiated with a 750 W tungsten lamp to undergo reaction at a temperature of 20° to 27° C. for 1 hour. Thereafter the reaction liquid was poured into ice water to separate the methylene chloride layer. The methylene chloride layer was washed successively with an aqueous solution of sodium thiosulfate and a saturated aqueous solution of sodium chloride and dried over anhydrous sodium sulfate. The solvent was distilled off at reduced pressure. The residue was purified by silica gel column chromatography using a 9:1 benzene-ethyl acetate mixture, giving 50.05 mg of a compound (Ib) wherein $R^1$ is Ph, $R^3$ is $CH_3$, and $X^1$, $X^2$, $X^3$ and $X^4$ are Cl. Yield 86%.

IR (cm$^{-1}$) 1770, 1760.

NMR (CDCl$_3$, δ, ppm) 3.80 (s, 3H), 3.89 (bs, 2H), 4.12 (s, 2H), 5.12 (s, 1H), 6.10 (d, 1H), 6.28 (d, 1H), 7.2–7.5 (m, 3H), 7.5–7.8 (m, 2H).

EXAMPLE 5

The procedure described in Example 4 was repeated with the exception of using carbon disulfide in place of the methylene chloride, giving 47.43 mg of a compound (Ib) wherein $R^1$ is Ph, $R^3$ is $CH_3$, and $X^1$, $X^2$, $X^3$ and $X^4$ are Cl in a yield of 81.5%. The compound was identified by IR and NMR.

EXAMPLE 6

The procedure of Example 4 was repeated by replacing the methylene chloride with ethyl acetate, giving 47.72 mg of a compound (Ib) wherein $R^1$ is Ph, $R^3$ is $CH_3$, and $X^1$, $X^2$, $X^3$ and $X^4$ are Cl. Yield 82.0%. The compound was identified by IR and NMR.

EXAMPLE 7

The procedure of Example 4 was repeated by using a compound (Ia) wherein $R^1$ is PhO, $R^3$ is $CH_3$, $X^1$ and $X^2$ are H, and $X^3$ is Cl, giving 60.19 mg of a compound (Ib) wherein $R^1$ is PhO, $R^3$ is $CH_3$, $X^1$ and $X^2$ are H, and $X^3$ and $X^4$ are Cl. Yield 88%.

IR (cm$^{-1}$) 1782, 1750.

NMR (CDCl$_3$, δ, ppm) 3.80 (s, 3H), 4.18 (bs, 4H), 5.16 (s, 1H), 6.00 (d, 1H), 6.35 (d, 1H), 6.16–7.50 (m, 5H).

EXAMPLE 8

The procedure of Example 4 was repeated by using 50 mg of a compound (Ia) wherein $R^1$ is Ph, $R^3$ is PhCH$_2$, and $X^1$, $X^2$ and $X^3$ are Cl, giving 53.38 mg of a compound (Ib) wherein $R^1$ is Ph, $R^3$ is PhCH$_2$, and $X^1$, $X^2$, $X^3$ and $X^4$ are Cl. Yield 93%.

IR (CHCl$_3$, cm$^{-1}$) 1782, 1743.

NMR (CDCl$_3$, δ, ppm) 3.88 (bs, 2H), 4.10 (s, 2H), 5.17 (s, 1H), 5.21 (s, 2H), 6.04 (d, 1H), 6.21 (d, 1H), 7.08–7.83 (m, 10H).

EXAMPLE 9

In 10 ml of methylene chloride was dissolved 50 mg of a compound (Ia) wherein $R^1$ is Ph, $R^3$ is CH$_3$, and $X^1$, $X^2$ and $X^3$ are Cl. To the solution was added 7 ml of a saturated aqueous solution of sodium chloride and 0.2 ml of conc. sulfuric acid. The mixture was then stirred. By using platinum electrodes (1.5×2 cm), electrolysis was continued at room temperature for 3 hours while the solution was stirred and irradiated with a 750 W tungsten lamp. Thereafter the methylene chloride layer was separated from the reaction mixture. The aqueous layer was extracted with methylene chloride. The extract was added to the methylene chloride layer and was dried over anhydrous sodium sulfate. The solvent was distilled off at reduced pressure. The residue was purified by silica gel column chromatography using a 9:1 benzene-ethyl acetate mixture as a developer, giving 57.03 mg of a compound (Ib) wherein $R^1$ is Ph, $R^3$ is CH$_3$, and $X^1$, $X^2$, $X^3$ and $X^4$ are Cl. Yield 98%. The compound (Ib) was identified by IR and NMR with the results identical with those obtained in Example 4.

EXAMPLE 10

In 8 ml of methylene chloride was dissolved 50 mg of a compound (Ia) wherein $R^1$ is Ph, $R^3$ is CH$_3$, and $X^1$, $X^2$ and $X^3$ are Cl. An H-type electrolytic bath divided into anode and cathode compartments by a diaphragm was charged with the solution in the former compartment and with 8 ml of methylene chloride in the latter. Then 7.8 ml of a saturated aqueous solution of sodium chloride and 0.2 ml of conc. sulfuric acid were placed into the anode and cathode compartments, respectively. The subsequent procedure of Example 9 produced 56.44 mg of a compound (Ib) wherein $R^1$ is Ph, $R^3$ is CH$_3$, and $X^1$, $X^2$, $X^3$ and $X^4$ are Cl. Yield 97%. The compound (Ib) was identified by IR and NMR with the results identical with those obtained in Example 4.

EXAMPLE 11

The procedure of Example 9 was followed by using ethyl acetate in place of the methylene chloride, giving 55.86 mg of a compound (Ib) wherein $R^1$ is Ph, $R^3$ is CH$_3$, and $X^1$, $X^2$, $X^3$ and $X^4$ are Cl. Yield 96%. The compound thus prepared was identified by IR and NMR with the results identical with those obtained in Example 4.

EXAMPLE 12

The procedure of Example 9 was repeated by using 7 ml of 1% hydrochloric acid in place of the saturated aqueous solution of sodium chloride and sulfuric acid, affording 56.15 mg of a compound (Ib) wherein $R^1$ is Ph, $R^3$ is CH$_3$, and $X^1$, $X^2$, $X^3$ and $X^4$ are Cl. Yield 96.5%. The compound thus prepared was identified by IR and NMR with the results identical with those obtained in Example 4.

EXAMPLE 13

The procedure of Example 9 was repeated by using 50 mg of a compound (Ia) wherein $R^1$ is PhO, $R^3$ is CH$_3$, and $X^1$, $X^2$ and $X^3$ are Cl, giving 64.64 mg of a compound (Ib) wherein $R^1$ is PhO, $R^3$ is CH$_3$, and $X^1$, $X^2$, $X^3$ and $X^4$ are Cl. Yield 94.5%. The compound thus produced was identified by IR and NMR with the results identical with those obtained in Example 7.

EXAMPLE 14

The procedure of Example 9 was repeated by using a compound (Ia) wherein $R^1$ is Ph, $R^3$ is PhCH$_2$ and $X^1$, $X^2$ and $X^3$ are Cl, giving 55.68 mg of a compound (Ib) wherein $R^1$ is Ph, $R^3$ is PhCH$_2$, and $X^1$, $X^2$, $X^3$ and $X^4$ are Cl. Yield 97%. The compound thus prepared was identified by IR and NMR with the results identical with those obtained in Example 8.

EXAMPLES 15–26

Each procedure described in Examples 4 to 14 was repeated by using compounds (Ia) shown in Tables 1 and 2 below, giving compounds (Examples 15 to 22) having the formula

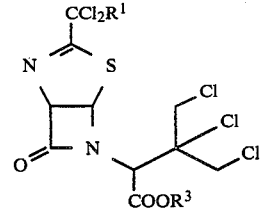

wherein $R^1$ and $R^3$ are as defined in Table 1 with the properties indicated therein and compounds (Examples 23 to 26) having the formula

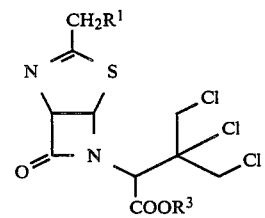

wherein $R^1$ and $R^3$ are as defined in Table 2 with the properties indicated therein.

TABLE 1

| Example | R¹ | R³ | IR (cm⁻¹) | NMR (δ, ppm) |
|---|---|---|---|---|
| 15 | Ph | $-CH_2-\phantom{x}\langle$C₆H₄$\rangle-NO_2$ (para) | 1770, 1730, 1525 | 3.90 (bs, 2H), 4.14 (bs, 2H, 5.20 (s, 1H), 5.25 (s, 2H), 6.05 (d, 4Hz), 6.24 (d, 4Hz), 7.0–7.8 (m, 5H), 7.50 (d, 9.0Hz), 8.20 (d, 9.0Hz) |
| 16 | Ph | $-CH_2CCl_3$ | 1770, 1743 | 4.02 (bs, 2H), 4.35 (bs, 2H), 4.82 (bs, 2H), 5.24 (s, 1H), 6.15 (d, 4.0Hz), 6.36 (d, 4.0Hz) 7.2–7.8 (m, 5H) |
| 17 | Ph | $-CHPh_2$ | 1780, 1745 | 3.85 (bs, 2H), 4.20 (bs, 2H), 5.17 (s, 1H), 5.90 (d, 4Hz), 6.22 (d, 4Hz), 6.95 (s, 1H), 7.0–8.0 (m, 15H) |
| 18 | PhO | $-CH_2-\langle C_6H_4\rangle-NO_2$ (para) | 1780, 1750, 1520 | 4.01 (bs, 2H), 4.20 (bs, 2H), 5.20 (s, 1H), 5.30 (s, 2H), 6.03 (d, 4Hz), 6.32 (d, 4Hz) 6.5–7.5 (m, 5H), 7.47 (d, 9Hz), 8.20 (d, 9Hz) |
| 19 | PhO | $-CH_2CCl_3$ | 1785, 1750 | 4.15 (bs, 2H), 4.25 (bs, 2H), 4.80 (bs, 2H), 5.25 (s, 1H), 6.10 (d, 4.0Hz), 6.38 (d, 4.0Hz), 6.5–7.5 (m, 5H) |
| 20 | PhO | $-CHPh_2$ | 1780, 1745 | 3.90 (bs, 2H), 4.30 (bs, 2H), 5.23 (s, 1H), 5.95 (d, 4Hz), 6.30 (d, 4Hz), 6.92 (s, 1H), 7.0–8.0 (m, 15H) |
| 21 | Ph | $-C(CH_3)_3$ | 1780, 1740 | 1.45 (s, 9H), 3.95 (bs, 2H), 4.35 (bs, 2H), 5.20 (s, 1H), 6.05 (d, 4.5Hz), 6.27 (d, 4.5Hz), 7.0–7.5 (m, 3H), 7.5–7.9 (m, 2H) |
| 22 | PhO | $-C(CH_3)_3$ | 1775, 1740 | 1.45 (s, 9H), 4.00 (bs, 2H), 4.45 (bs, 2H), 5.25 (s, 1H), 6.00 (d, 4.0Hz), 6.30 (d, 4.0Hz), 6.5–7.5 (m, 5H) |

TABLE 2

| Example | R¹ | R³ | IR (cm⁻¹) | NMR (δ, ppm) |
|---|---|---|---|---|
| 23 | Ph | $-CH_2-\langle C_6H_4\rangle-NO_2$ (para) | 1770, 1735, 1525 | 3.80 (s, 2H), 3.95 (bs, 2H), 4.20 (bs, 2H), 5.20 (s, 1H), 5.28 (s, 2H), 6.00 (bs, 4Hz), 6.22 (d, 4Hz), 7.25 (bs, 5H), 7.50 (d, 9.5Hz), 8.15 (d, 9.5Hz) |
| 24 | Ph | $-CH_2CCl_3$ | 1775, 1740 | 3.82 (s, 2H), 4.00 (bs, 2H), 4.45 (bs, 2H), 4.80 (bs, 2H), 5.20 (s, 1H), 6.10 (bs, 4Hz), 6.29 (d, 4Hz), 7.23 (bs, 5H) |
| 25 | Ph | $-CHPh_2$ | 1780, 1740 | 3.90 (bs, 4H), 4.25 (bs, 2H), 5.15 (s, 1H), 5.95 (bd, 4Hz), 6.30 (d, 4Hz), 6.95 (s, 1H), 7.0–8.0 (m, 15H) |
| 26 | Ph | $-C(CH_3)_3$ | 1780, 1745 | 1.45 (s, 9H), 3.85 (bs, 2H), 4.00 (bs, 2H), 4.25 (bs, 2H), 5.15 (s, 1H), 5.90 (bd, 4.5Hz), 6.15 (d, 4.5Hz), 7.25 (bs, 5H) |

EXAMPLE 27

There were mixed together 886 mg of a compound (Ib) wherein $R^1$ is Ph, $R^3$ is $CH_3$, and $X^1$, $X^2$, $X^3$ and $X^4$ are Cl, 264 mg of zinc powder and 11.5 ml of methylene chloride. The mixture was cooled to 0° to −5° C. Thereto was added 3.3 ml of acetic acid, and the resulting mixture was stirred for 30 minutes. Thereafter 15 ml of ether was added with cooling to the reaction mixture to separate the organic layer. The organic layer was then washed successively with water, a saturated aqueous solution of sodium hydrogencarbonate and a saturated aqueous solution of sodium chloride and dried over anhydrous sodium sulfate. The solvent was distilled off at reduced pressure. The residue was purified by silica gel column chromatography using a 10:1 benzene-ethyl acetate mixture as a developer, affording a compound (Ib) wherein $R^1$ is Ph, $R^3$ is $CH_3$, $X^1$ and $X^2$ and H, and $X^3$ and $X^4$ are Cl. Yield 95%.

IR (CHCl₃, cm⁻¹) 1770, 1740.

NMR (CDCl₃, δ, ppm) 3.74 (s, 3H), 3.89 (bs, 4H), 4.14 (s, 2H), 5.07 (s, 1H), 5.95 (bd, 1H, J=4.5 Hz), 6.12 (d, 1H, J=4.5 Hz) 7.23 (s, 5H).

EXAMPLE 28

To 0° to −5° C. was cooled a mixture of 50 mg of a compound (Ib) wherein $R^1$ is Ph, $R^3$ is $CH_3$, and $X^1$, $X^2$, $X^3$ and $X^4$ are Cl, 15 mg of zinc powder and 0.7 ml of ethyl acetate. Thereto was added 0.2 ml of acetic acid and the mixture was stirred for 30 minutes. The subsequent procedure of Example 27 produced a compound (Ib) wherein $R^1$ is Ph, $R^3$ is $CH_3$, $X^1$ and $X^2$ are H, and $X^3$ and $X^4$ are Cl. Yield 96.5%. The compound was identified by IR and NMR with the results identical with those obtained in Example 27.

EXAMPLE 29

To 0° to −5° C. was cooled a mixture of 50 mg of a compound (Ib) wherein $R^1$ is Ph, $R^3$ is PhCH₂, and $X^1$, $X^2$, $X^3$ and $X^4$ are Cl, 12.4 mg of zinc powder and 0.7 ml of methylene chloride. The resulting mixture was stirred for 30 minutes. The subsequent procedure of Example 27 produced a compound (Ib) wherein $R^1$ is Ph, $R^3$ is PhCH₂, $X^1$ and $X^2$ are H, and $X^3$ and $X^4$ are Cl. Yield 94%.

IR (CHCl₃, cm⁻¹) 1780, 1740.

NMR (CDCl$_3$, δ, ppm) 3.82 (s, 2H), 3.88 (bs, 2H), 4.05 (s, 2H), 5.12 (s, 1H), 5.20 (s, 2H), 5.90 (bd, 1H, J=4.2 Hz), 6.07 (d, 1H, J=4.2 Hz), 7.25 (bs, 10H).

EXAMPLE 30

In 0.6 ml of methyl chloride was dissolved 55 mg of a compound (Ib) wherein $R^1$ is Ph, $R^3$ is CH$_3$, $X^1$ and $X^2$ are H, and $X^3$ and $X^4$ are Cl. Thereto was added 88 μl of triethylamine. The mixture was stirred at room temperature for 2 hours. Thereafter 5 ml of ether was added to the reaction mixture. Then the mixture was washed successively with water, 10% hydrochloric acid and then a saturated aqueous solution of sodium chloride. The ether layer was dried over anhydrous sodium sulfate. The solvent was distilled off at reduced pressure. The residue was purified by silica gel column chromatography, giving a colorless oily product, namely a compound (Ic) wherein $R^1$ is Ph, $R^3$ is CH$_3$, $X^1$ and $X^2$ are H, and $X^4$ and $X^5$ are Cl. Yield 98%.

IR (cm$^{-1}$) 1770, 1720.

NMR (CDCl$_3$, δ, ppm) 3.76 (s, 3H), 3.90 (s, 2H), 4.07 (bs, 2H), 4.63 (bs, 2H), 5.83 (d, 1H), 6.03 (bd, 1H), 7.25 (s, 5H).

EXAMPLES 31 TO 36

The procedure of Example 30 was followed by using compounds (Ib) shown in Table 3 below and employing the conditions indicated therein, giving compounds (Ic) tabulated in Table 4 below in the yeilds and with the properties listed in Tables 3 and 4, respectively.

TABLE 3

| Ex. | Compound (Ib) | | | | | | | Solvent | Base | Temp. | Time (hrs.) | Yield (%) |
| --- | --- | --- | --- | --- | --- | --- | --- | --- | --- | --- | --- | --- |
| | $R^1$ | $R^3$ | $X^1$ | $X^2$ | $X^3$ | $X^4$ | mg | | | | | |
| 31 | Ph | CH$_3$ | H | H | Cl | Cl | 55 | THF* (0.6 ml) | TEA* (88 μl) | Room temp. | 2 | 97 |
| 32 | Ph | CH$_3$ | H | H | Cl | Cl | 55 | CH$_2$Cl$_2$ (0.6 ml) | EDIA* (110 μl) | Room temp. | 2 | 94 |
| 33 | Ph | CH$_3$ | Cl | Cl | Cl | Cl | 53 | CH$_2$Cl$_2$ (0.5 ml) | TEA (74 μl) | Room temp. | 2 | 93 |
| 34 | Ph | PhCH$_2$ | Cl | Cl | Cl | Cl | 86 | CH$_2$Cl$_2$ (2 ml) | TEA (100 μl) | Room temp. | 2 | 96 |
| 35 | Ph | PhCH$_2$ | H | H | Cl | Cl | 40 | CH$_2$Cl$_2$ (0.5 ml) | TEA (30 μl) | Room temp. | 2 | 97.5 |
| 36 | PhO | CH$_3$ | Cl | Cl | Cl | Cl | 55 | CH$_2$Cl$_2$ (0.8 ml) | TEA (37 μl) | Room temp. | 2 | 98 |

*EDIA = ethyl diisopropylamine
THF = tetrahydrofuran
TEA = triethylamine

TABLE 4

| Ex. | Compound (Ic) | | | | | | IR (cm$^{-1}$) | $^1$H—NMR (δ, ppm) |
| --- | --- | --- | --- | --- | --- | --- | --- | --- |
| | $R^1$ | $R^3$ | $X^1$ | $X^2$ | $X^4$ | $X^5$ | | |
| 31 | Ph | CH$_3$ | H | H | Cl | Cl | Same as in Example 30 | Same as in Example 30 |
| 32 | Ph | CH$_3$ | H | H | Cl | Cl | Same as in Example 30 | Same as in Example 30 |
| 33 | Ph | CH$_3$ | Cl | Cl | Cl | Cl | 1765 1735 | 3.83 (s, 3H), 4.10 (bs, 2H), 4.67 (s, 2H), 5.94 (d, 1H, J = 4.5 Hz), 6.16 (d, 1H, J = 4.5 Hz), 7.2–7.55 (m, 3H), 7.55–7.9 (m, 2H) |
| 34 | Ph | PhCH$_2$ | Cl | Cl | Cl | Cl | 1782 1727 | 3.94 (d, 1H, J = 11 Hz), 4.16 (d, 1H, J = 11 Hz), 4.48 (d, 1H, J = 12 Hz), 4.70 (d, 1H, J = 12 Hz), 5.08 (d, 1H, J = 11 Hz), 5.30 (d, 1H, J = 11 Hz), 5.77 (d, 1H, J = 4.5 Hz), 6.02 (d, 1H, J = 4.5 Hz), 7.1–7.9 (m, 10H) |
| 35 | Ph | PhCH$_2$ | H | H | Cl | Cl | 1780 1725 | 3.89 (s, 2H), 4.06 (bs, 2H), 4.64 (bs, 2H), 5.78 (d, 1H, J = 4.3 Hz), 6.03 (bd, 1H, J = 4.3 Hz), 7.30 (bs, 10H) |
| 36 | PhO | CH$_3$ | Cl | Cl | Cl | Cl | 1780 1730 | 3.85 (s, 3H), 4.30 (bs, 2H), 4.71 (bs, 2H), 6.05 (m, 2H), 6.7–7.5 (m, 5H) |

EXAMPLES 37 TO 48

Compounds (Ic) as shown in Table 5 below were prepared by repeating the procedure of Example 30 with the exception of using the corresponding compounds (Ib) as the starting materials.

TABLE 5

| Ex. | Compound (Ic) | | | | | | IR (cm$^{-1}$) | $^1$H—NMR (δ, ppm) |
| --- | --- | --- | --- | --- | --- | --- | --- | --- |
| | $R^1$ | $R^3$ | $X^1$ | $X^2$ | $X^4$ | $X^5$ | | |
| 37 | Ph | Ph$_2$CH | Cl | Cl | Cl | Cl | 1780 1750 | 3.90 (bs, 2H), 4.45 (bs, 2H), 5.90 (d, 1H, 4.5 Hz), 6.22 (d, 1H, 4.5 Hz), 6.95 (s, 1H), 7.0–8.0 (m, 15H) |
| 38 | Ph | Ph$_2$CH | H | H | Cl | Cl | 1780 | 3.90 (bs, 4H), 4.50 (bs, 2H), |

TABLE 5-continued

| Ex. | Compound (Ic) R$^1$ | R$^3$ | X$^1$ | X$^2$ | X$^4$ | X$^5$ | IR (cm$^{-1}$) | $^1$H—NMR (δ, ppm) |
|---|---|---|---|---|---|---|---|---|
| | | | | | | | 1740 | 5.94 (d, 1H, 4.5 Hz), 6.26 (bd, 1H, 4.5 Hz), 6.95 (s, 1H), 7.0–8.0 (m, 15H) |
| 39 | PhO | p-NO$_2$PhCH$_2$ | Cl | Cl | Cl | Cl | 1780 1750 | 4.12 (bs, 2H), 4.61 (bs, 2H), 5.25 (bs, 2H), 5.67 (d, 1H, 4.5 Hz), 6.00 (d, 1H, 4.5 Hz), 6.5–7.5 (m, 5H), 7.47 (d, 2H, 9 Hz), 8.15 (d, 2H, 9 Hz) |
| 40 | PhO | CCl$_3$CH$_2$ | Cl | Cl | Cl | Cl | 1784 1750 | 4.15 (bs, 2H), 4.65 (bs, 2H), 4.80 (bs, 2H), 5.98 (d, 1H, 4.5 Hz), 6.20 (d, 1H, 4.5 Hz), 6.5–7.5 (m, 5H) |
| 41 | PhO | t-C$_4$H$_9$ | Cl | Cl | Cl | Cl | 1780 1745 | 1.47 (bs, 9H), 4.05 (bs, 2H), 4.64 (bs, 2H), 5.90 (d, 1H, 4.5 Hz), 6.13 (d, 1H, 4.5 Hz), 6.9–7.80 (m, 5H) |
| 42 | PhO | Ph$_2$CH | Cl | Cl | Cl | Cl | 1778 1750 | 3.95 (bs, 2H), 4.50 (bs, 2H), 5.95 (d, 1H, 4.5 Hz), 6.29 (d, 1H, 4.5 Hz), 6.93 (s, 1H), 7.0–8.0 (m, 15H) |
| 43 | Ph | p-NO$_2$PhCH$_2$ | Cl | Cl | Cl | Cl | 1770 1730 1525 | 4.10 (bs, 2H), 4.67 (bs, 2H), 5.29 (bs, 2H), 5.70 (d, 1H, J = 4.5 Hz), 6.01 (d, 1H, J = 4.5 Hz), 7.47 (d, 2H, J = 8 Hz), 8.15 (d, 2H, J = 8 Hz), 7.15–8.00 (m, 5H) |
| 44 | Ph | p-NO$_2$PhCH$_2$ | H | H | Cl | Cl | 1770 1735 1525 | 3.98 (s, 2H), 4.07 (bs, 2H), 4.63 (bs, 2H), 5.18 (bs, 2H), 5.69 (d, 1H, J = 4.5 Hz), 6.00 (bd, 1H, J = 4.5 Hz), 7.47 (d, 2H, J = 8 Hz), 8.15 (d, 2H, J = 8 Hz), 7.25 (s, 5H) |
| 45 | Ph | CCl$_3$CH$_2$ | Cl | Cl | Cl | Cl | 1770 1740 | 4.16 (bs, 2H), 4.72 (bs, 2H), 4.78 (bs, 2H), 5.95 (d, 1H, J = 4.5 Hz), 6.17 (d, 1H, J = 4.5 Hz), 7.10–7.90 (m, 5H) |
| 46 | Ph | CCl$_3$CH$_2$ | H | H | Cl | Cl | 1775 1745 | 3.90 (s, 2H), 4.13 (bs, 2H), 4.69 (bs, 2H), 4.75 (bs, 2H), 5.93 (d, 1H, J = 4.5 Hz), 6.16 (bd, 1H, J = 4.5 Hz), 7.23 (s, 5H) |
| 47 | Ph | t-C$_4$H$_9$ | Cl | Cl | Cl | Cl | 1780 1743 | 1.47 (s, 9H), 4.08 (bs, 2H), 4.62 (bs, 2H), 5.94 (d, 1H, J = 4.5 Hz), 6.15 (d, 1H, J = 4.5 Hz), 7.1–7.9 (m, 5H) |
| 48 | Ph | t-C$_4$H$_9$ | H | H | Cl | Cl | 1780 1745 | 1.45 (s, 9H), 3.88 (s, 2H), 4.07 (bs, 2H), 4.60 (bs, 2H), 5.95 (d, 1H, J = 4.5 Hz), 6.14 (bd, 1H, J = 4.5 Hz), 7.25 (s, 5H) |

EXAMPLE 49

To 0° to −5° C. was cooled a mixture of 50 mg of a compound (Ic) wherein R$^1$ is Ph, R$^3$ is CH$_3$, and X$^1$, X$^2$, X$^4$ and X$^5$ are Cl, 14 mg of zinc powder and 0.7 ml of methylene chloride. Thereto was added 0.2 ml of acetic acid. The mixture was stirred for 30 minutes. Thereafter 15 ml of ether was added to the reaction mixture with cooling to separate the organic layer. Then the organic layer was washed successively with water, a saturated aqueous solution of sodium hydrogencarbonate and a saturated aqueous solution of sodium chloride, and dried over anhydrous sodium sulfate. The solvent was distilled off at reduced pressure. The purification of the residue by silica gel column chromatography using a 10:1 benzene-ethyl acetate produced a compound (Ic) wherein R$^1$ is Ph, R$^3$ is CH$_3$, X$^1$ and X$^2$ are H, and X$^4$ and X$^5$ are Cl. Yield 91%.

IR (CHCl$_3$, cm$^{-1}$) 1770, 1720.

NMR (CDCl$_3$, δ, ppm) 3.76 (s, 3H), 3.90 (s, 2H), 4.07 (bs, 2H), 4.63 (bs, 2H), 5.83 (d, 1H, J=4.5 Hz), 6.03 (bd, 1H, J=4.5 Hz), 7.25 (s, 5H).

EXAMPLE 50

To 0° to −5° C. was cooled a mixture of 50 mg of a compound (Ic) wherein R$^1$ is Ph, R$^3$ is PhCH$_2$, and X$^1$, X$^2$, X$^4$ and X$^5$ are Cl, 15.2 mg of zinc powder and 0.2 ml of methylene chloride, to which 0.2 ml of acetic acid was added. The resulting mixture was stirred for 30 minutes. The subsequent procedure of Example 49 produced a compound (Ic) wherein R$^1$ is Ph, R$^3$ is PhCH$_2$, X$^1$ and X$^2$ are H, and X$^4$ and X$^5$ are Cl. Yield 95%.

IR (CHCl$_3$, cm$^{-1}$) 1780, 1725.

NMR (CDCl$_3$, δ, ppm) 3.89 (s, 2H), 4.06 (bs, 2H), 4.64 (bs, 2H), 5.78 (d, 1H, J=4.3 Hz), 6.03 (bd, 1H, J=4.3 Hz), 7.30 (bs, 10H).

EXAMPLE 51

In 1.3 ml of dioxane was dissolved 65 mg of the ester of 2-(3-benzyl-7-oxo-4-thia-2,6-diazabicyclo[3,2,0]hepta-2-ene-6-yl)-3-chloromethyl-3-butenoic acid and benzyl alcohol represented by the formula

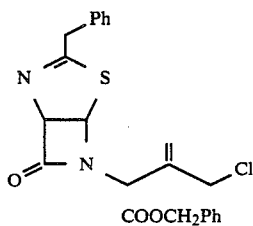

COOCH₂Ph to obtain a uniform solution to which was then added 0.13 ml of water.

A reactor was charged with 98 mg of 2-benzothiazolyldisulfide and 5 ml of dioxane, and was heated by being dipped in a hot-water bath to prepare a uniform solution to which was added 0.40 ml of a carbon tetrachloride solution of chlorine. The reactor was shaken awhile. Then the contents of the reactor were added to the foregoing dioxane solution, and stirred at room temperature for 30 minutes. The resulting reaction mixture was diluted with 20 ml of ethyl acetate. The dilute solution was washed with a saturated aqueous solution of sodium chloride, dried over Na₂SO₄ and concentrated. The residue was subjected to silica gel chromatography using a 8:1 benzene-ethyl acetate mixture as a developer, giving 81.5 mg of the ester of 2-(3-phenylacetamide-4-(2-benzothiazolyldithio)-2-azetidinone-1-yl)-3-chloromethyl-3-butenoic acid and benzyl alcohol, having the formula

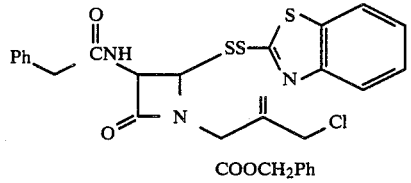

COOCH₂Ph

Yield 91%. The compound thus prepared was analyzed with the following results.

NMR (δ, CDCl₃, ppm) 3.66 (s, 2H), 4.15 and 4.39 (ABq, 2H, 11 Hz), 5.14 (s, 2H), 5.0–5.4 (m, 3H), 5.50 (s, 1H), 5.55 (d, 1H, 4 Hz), 6.92 (d, 1H, 8 Hz), 7.1–7.6 (m, 12H), 7.6–8.0 (m, 2H).

EXAMPLES 52 TO 63

Compounds (IV) wherein $R^1$, $R^3$ and $R^4$ are as defined in Table 6 below were prepared in the same manner as in Example 51 from the corresponding compounds (Ia) in the yields and with the properties tabulated in Table 6.

TABLE 6

| Ex. | $R^1$ | $R^3$ | $R^4$ | Yield | NMR (δ, CDCl₃, ppm) |
|-----|-------|-------|-------|-------|---------------------|
| 52 | Ph | CH₃ | n-Bu | 69 | 0.95 (bt, 3H, 6Hz), 1.2–1.8 (m, 4H), 2.61 (bt, 2H, 6Hz), 3.64 (s, 2H), 3.78 (s, 3H), 4.19 (bs, 2H), 5.06 (s, 1H), 5.15–5.6 (m, 4H), 6.40 (d, 1H, 8Hz), 7.2–7.4 (m, 5H) |
| 53 | Ph | CH₃ | Ph | 56 | 3.51 (s, 2H), 3.68 (s, 3H), 4.10 (bs, 2H), 4.94 (s, 1H), 5.11 (s, 1H), 5.2–5.5 (m, 3H), 6.12 (d, 1H, 8Hz), 7.1–7.6 (m, 10H) |
| 54 | Ph | CH₃ | p-NO₂-C₆H₄ | 50 | 3.70 (s, 2H), 3.80 (s, 3H), 4.27 (bs, 2H), 5.17 (s, 1H), 5.25–5.45 (m, 3H), 5.61 (s, 1H), 6.72 (bd, 1H, 8Hz), 7.37 (s, 5H), 7.51 (d, 2H, 9Hz), 8.12 (d, 2H, 9Hz) |
| 55 | Ph | CH₃ | 2-pyridyl | 78 | 3.55 (s, 2H), 3.71 (s, 3H), 4.24 (bs, 2H), 5.18 (s, 1H), 5.25–5.5 (m, 3H), 5.48 (s, 1H), 7.0–7.65 (m, 8H), 8.40 (bd, 5.5Hz) |
| 56 | Ph | CH₃ | 5-methyl-1,3,4-thiadiazol-2-yl | 49 | 2.70 (s, 3H), 3.66 (s, 2H), 3.79 (s, 3H), 4.26 (bs, 2H), 5.05–5.35 (m, 3H), 5.56 (s, 1H), 5.62 (d, 1H, 4.5Hz), 7.00 (d, 1H, 9Hz), 7.32 (s, 5H) |
| 57 | Ph | CH₃ | 1-methyl-1H-tetrazol-5-yl | 45 | 3.60 (s, 2H), 3.77 (s, 3H), 3.97 (s, 3H), 4.24 (bs, 2H), 5.10 (dd, 1H, 5Hz, 8Hz), 5.21 (s, 2H), 5.47 (s, 1H), 5.66 (d, 1H, 5Hz) |
| 58 | Ph | CH₃ | 2-benzothiazolyl | 76 | 3.69 (s, 3H), 4.16 and 4.40 (ABq, 2H, 12Hz), 5.21 (dd, 1H, 5Hz, 8Hz), 5.30 (bs, 2H), 5.53 (d, 1H, 5H), 5.56 (s, 1H), 7.02 (d, 1H, 8Hz), 7.2–7.55 (m, 7H), 7.55–7.95 (m, 2H) |
| 59 | Ph | PhCH₂ | 5-methyl-1,3,4-thiadiazol-2-yl | 63 | 2.62 (s, 3H), 3.60 (s, 2H), 4.21 (bs, 2H), 5.16 (s, 2H), 5.05–5.4 (m, 3H), 5.46 (s, 1H), 5.55 (d, 1H, 4.5Hz), 7.1–7.45 (m, 11H) |

TABLE 6-continued

| Ex. | R¹ | R³ | R⁴ | Yield | NMR (δ, CDCl₃, ppm) |
|---|---|---|---|---|---|
| 60 | Ph | PhCH₂ | 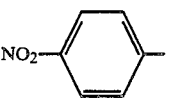 | 61 | 3.65 (s, 2H), 4.22 (bs, 2H), 5.20 (s, 2H), 5.05–5.4 (m, 4H), 5.53 (s, 1H), 6.81 (bd, 1H, 8Hz), 7.34 (s, 10H), 7.42 (d, 2H, 9Hz), 8.05 (d, 2H, 9Hz) |
| 61 | Ph | PhCH₂ | 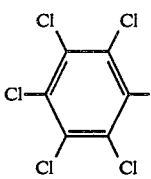 | 35 | 3.55 (s, 2H), 4.24 (bs, 2H), 4.96 (s, 1H), 5.05–5.4 (m, 3H), 5.27 (s, 2H), 5.68 (d, 1H, 5Hz), 6.16 (d, 1H, 8Hz), 7.15–7.45 (m, 10H) |
| 62 | Ph | PhCH₂ | 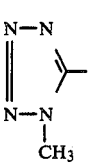 | 45 | 3.64 (s, 2H), 3.93 (s, 3H), 4.21 (bs, 2H), 5.0–5.7 (m, 5H), 5.20 (s, 2H), 6.95 (d, 1H, 8.5Hz), 7.15–7.4 (m, 10H) |
| 63 | PhO | PhCH₂ | Ph— | 57 | 4.20 (bs, 2H), 4.55 (s, 2H), 4.9–5.5 (m, 5H), 5.20 (s, 2H), 6.7–7.9 (m, 16H) |

EXAMPLE 64

The procedure of Example 51 was repeated replacing the dioxane as a solvent with dimethyl sulfoxide, giving the ester of 2-(3-phenylacetamide-4-(2-benzothiazolyldithio)-2-azetidinone-1-yl)-3-chloromethyl-3-butenoic acid and benzyl alcohol. Yield 89%. The compound was analyzed with the results identical with those obtained in Example 51.

EXAMPLE 65

In 1.5 ml of dioxane was dissolved 50 mg of the ester of 2-(3-benzyl-7-oxo-4-thia-2,6-diazabicyclo[3,2,0]hepta-2-ene-6-yl)-3-chloromethyl-3-butenoic acid and benzyl alcohol to obtain a uniform solution to which 0.15 ml of water was added.

A reactor was charged with 42 mg of 2-benzothiazolyldifulfide, 32 mg of iodine and 5 ml of dioxane and heated by being dipped in a hot-water bath to obtain a uniform solution which was added to the foregoing dioxane solution to undergo reaction at room temperature for 30 minutes. The resulting reaction mixture was treated in the same manner as in Example 51, giving the ester of 2-(3-phenylacetamide-4-(2-benzothiazolyldithio)-2-azetidinone-1-yl)-3-chloromethyl-3-butenoic acid and benzyl alcohol. Yield 80%.

The compound thus prepared was analyzed with the results identical with those obtained in Example 51.

EXAMPLE 66

(1) In 0.5 ml of dimethylformamide was dissolved 30 mg of the ester of 2-(3-phenylacetamide-4-(2-benzothiazolyldithio)-2-azetidinone-1-yl)-3-chloromethyl-3-butenoic acid and benzyl alcohol having the formula

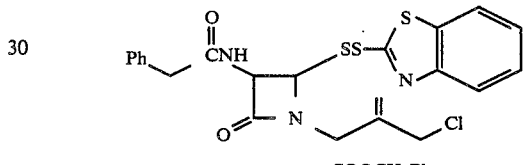

to obtain a uniform solution. The solution was cooled to −30° C. Thereto was added 40 μl of a solution (about 2 mole) of ammonia is dimethylformamide. The mixture was stirred for 1 hour and then 4 drops of 5% hydrochloric acid were added thereto. The mixture was vigorously agitated until it had room temperature. Then the mixture was diluted with 5 ml of ethyl acetate. The dilute solution was washed with a saturated aqueous solution of sodium chloride, dried over Na₂SO₄ and concentrated. The residue was subjected to silica gel column chromatography using a 15:1 benzene-ethyl acetate mixture, affording 24.4 mg of the ester of 7-phenylacetamide-3-(benzothiazole-2-yl-thiomethyl)-3-cephem-4-carboxylic acid and benzyl alcohol having the formula

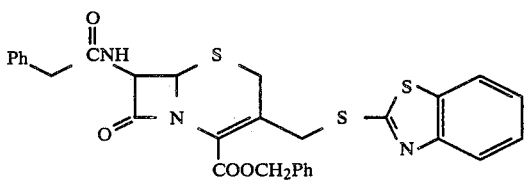

Yield 85%. The compound thus prepared was analyzed with the following results.

IR (Nujol, cm⁻¹) 3315, 1765, 1715, 1655.

NMR (δ, CDCl₃, ppm) 3.60 (s, 4H), 4.16 and 4.83 (ABq, 2H, 13 Hz), 4.88 (d, 1H, 5 Hz), 5.30 (s, 2H), 5.78 (dd, 1H, 5 Hz, 9 Hz), 6.38 (d, 1H, 9 Hz), 7.1–7.6 (m, 12H), 7.6–8.0 (m, 2H).

(2) In 0.6 ml of dimethylformamide was dissolved 43.6 mg of the ester of 2-(3-phenylacetamide-4-(2-benzothiazolyldithio)-2-azetidinone-1-yl)-3-chloromethyl-3-butenoic acid and benzyl alcohol to obtain a uniform solution. The solution was cooled to $-25°$ C., and 15 $\mu$l of 28% ammonia water was added thereto. The mixture was stirred for 1 hour and 30 minutes. Then 4 drops of 5% hydrochloric acid was added to the reaction mixture and vigorously agitated until it had room temperature. The mixture was diluted with 5 ml of ethyl acetate, washed with a saturated aqueous solution of sodium chloride, dried over $Na_2SO_4$ and concentrated. The purification of the residue by silica gel column chromatography using a 15:1 benzene-ethyl acetate mixture produced 29.3 mg of the ester of 7-phenylacetamide-3-(benzothiazole-2-yl-thiomethyl)-3-cephem-4-carboxylic acid and benzyl alcohol. Yield 72%. The compound thus prepared was analyzed with the results identical with those obtained in Example 66, (1).

EXAMPLES 67 TO 74

The procedure of Example 66 was repeated using the compounds (VI) shown in Table 7 below and employing the reaction conditions listed therein, giving compounds (VII) indicated in Table 8.

TABLE 7

| Ex. | Compound (VI) $R^1$ | $R^3$ | $R^4$ | Solvent | Reactant | Temp. (°C.) | Time (hrs.) | Yield (%) |
|---|---|---|---|---|---|---|---|---|
| 67 | Ph | PhCH$_2$ | benzothiazole | DMA | Ammonia gas | $-10$ | 1 | 61 |
| 68 | Ph | PhCH$_2$ | 5-methyl-1,3,4-thiadiazol-2-yl | DMF | Ammonia gas | $-25$ | 1 | 77 |
| 69 | Ph | PhCH$_2$ | 1-methyl-1H-tetrazol-5-yl | DMF | Ammonia gas | $-25$ | 1 | 74 |
| 70 | Ph | CH$_3$ | benzothiazole | DMF | Ammonia gas | $-25$ | 2 | 80 |
| 71 | Ph | CH$_3$ | benzothiazole | DMF | Ammonia gas | $-25$ | 2 | 81 |
| 72 | Ph | CH$_3$ | 5-methyl-1,3,4-thiadiazol-2-yl | DMF | Ammonia gas | $-25$ | 1 | 71 |
| 73 | Ph | CH$_3$ | 1-methyl-1H-tetrazol-5-yl | DMF | Ammonia gas | $-7$ | 1 | 45 |
| 74 | Ph | CH$_3$ | 1-methyl-1H-tetrazol-5-yl | DMA | Ammonia gas | $-7$ | 1 | 63 |

TABLE 8

| Ex. | Compound (VII) $R^1$ | $R^3$ | Y | IR (Nujol, cm$^{-1}$) | NMR ($\delta$, CDCl$_3$, ppm) |
|---|---|---|---|---|---|
| 67 | Ph | PhCH$_2$ | benzothiazol-2-yl-S— | Same as in Example 66 (1) | Same as in Example 66 (1) |

TABLE 8-continued

| Ex. | Compound (VII) R¹ | R³ | Y | IR (Nujol, cm$^{-1}$) | NMR (δ, CDCl₃, ppm) |
|---|---|---|---|---|---|
| 68 | Ph | PhCH₂ | CH₃-⟨S,N-N⟩-S- (thiadiazole with CH₃) | 3340, 1785, 1725, 1665 | 2.68 (s, 3H), 3.62 (s, 4H), 4.13 and 4.66 (ABq, 2H, 14Hz), 4.90 (d, 1H, 4.5Hz), 5.27 (s, 2H), 5.79 (dd, 1H, 4.5Hz, 9Hz), 6.27 (d, 1H, 9Hz), 7.30 (s, 5H), 7.36 (s, 5H) |
| 69 | Ph | PhCH₂ | N-N/N-N(CH₃) tetrazole-S- | 3265, 1780, 1710, 1655 | 3.65 (s, 2H), 3.70 (s, 2H), 3.90 (s, 3H), 4.24 and 4.53 (ABq, 2H, 14Hz), 4.95 (d, 1H, 5Hz), 5.31 (s, 2H), 5.85 (dd, 1H, 5Hz, 9Hz), 6.21 (d, 1H, 9Hz), 7.32 (s, 5H), 7.40 (s, 5H) |
| 70, 71 | Ph | CH₃ | benzothiazol-2-yl-S- | 3240, 1775, 1710, 1650 | 3.63 (s, 4H), 3.88 (s, 3H), 4.28 and 4.86 (ABq, 2H, 13Hz), 4.94 (d, 1H, 5Hz), 5.80 (dd, 1H, 5Hz, 9Hz), 6.32 (d, 1H, 9Hz), 7.15–7.55 (m, 12H), 7.55–7.95 (m, 2H) |
| 72 | Ph | CH₃ | CH₃-⟨S,N-N⟩-S- | 3270, 1780, 1710, 1655 | 2.72 (s, 3H), 3.63 (s, 4H), 3.85 (s, 3H), 4.12 and 4.65 (ABq, 2H, 13Hz), 4.91 (d, 1H, 5Hz), 5.79 (dd, 1H, 5Hz, 9Hz), 6.34 (d, 1H, 9Hz), 7.27 (s, 5H) |
| 73, 74 | Ph | CH₃ | N-N/N-N(CH₃) tetrazole-S- | 3260, 1775, 1705, 1650 | 3.67 (s, 2H), 3.71 (s, 2H), 3.88 (s, 3H), 3.92 (s, 3H), 4.25 and 4.54 (ABq, 2H, 14Hz), 4.96 (d, 1H, 5Hz), 5.86 (dd, 1H, 5Hz, 8.5Hz), 6.26 (d, 1H, 8.5Hz), 7.2–7.5 (m, 5H) |

EXAMPLE 75

The reaction in Example 75 is illustrated schematically as follows.

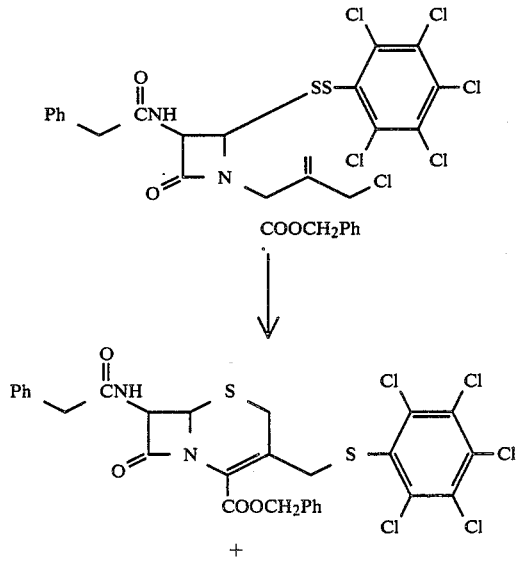

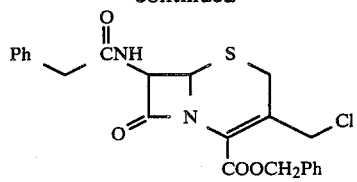

In 0.4 ml of dimethylformamide was dissolved 20 mg of the ester of 2-(3-phenylacetamide-4-pentachlorophenyldithio-2-azetidinone-1-yl)-3-chloromethyl-3-butenoic acid and benzyl alcohol to obtain a uniform solution. The solution was cooled to −25° C. and thereto was added 20 μl of a solution (about 20 mole) of ammonia gas in dimethylformamide. The mixture was stirred for 1 hour. After adding 3 drops of 5% hydrochloric acid thereto, the resulting mixture was vigorously agitated until it had room temperature. Then it was diluted with 5 ml of ethyl acetate. The dilute solution was washed with a saturated aqueous solution of sodium chloride, dried over Na₂SO₄ and concentrated. The residue was treated by silica gel column chromatography using a 10:1 benzene-ethyl acetate mixture, giving two compounds, namely (1) 6.6 mg of the ester of 7-phenylacetamide-3-pentachlorophenylthiomethyl-3-cephem-4-carboxylic acid and benzyl alcohol in a yield of 35% and (2) 5.5 mg of 7-phenylacetamide-3-chloromethyl-3-cephem-4-carboxylic acid and benzyl alcohol in a yield of 45%. These two compounds (1) and (2) were analyzed with the following results.

Compound (1)

IR (Nujol, cm$^{-1}$) 3250, 1775, 1710, 1650.

NMR (δ, CDCl₃, ppm) 3.36 and 3.80 (ABq, 2H, 18 Hz), 3.64 (s, 2H), 3.82 and 4.28 (ABq, 2H, 13 Hz), 4.94 and 5.20 (ABq, 2H, 13 Hz), 4.95 (d, 1H, 5 Hz), 5.77 (dd, 1H, 5 Hz, 9 Hz), 6.18 (d, 1H, 9 Hz), 7.37 (s, 5H).

Compound (2)

IR (Nujol, cm⁻¹) 1790, 1730, 1680.

NMR (δ, CDCl₃, ppm) 3.32 and 3.60 (ABq, 2H, 18 Hz), 3.53 (s, 2H), 4.31 and 4.45 (ABq, 2H, 12 Hz), 4.86 (d, 1H, 5 Hz), 5.20 (s, 2H), 5.77 (dd, 1H, 5 Hz, 9 Hz), 6.43 (d, 1H, 9 Hz), 7.27 (s, 5H), 7.33 (s, 5H).

EXAMPLE 76

The reaction in this example is illustrated schematically below.

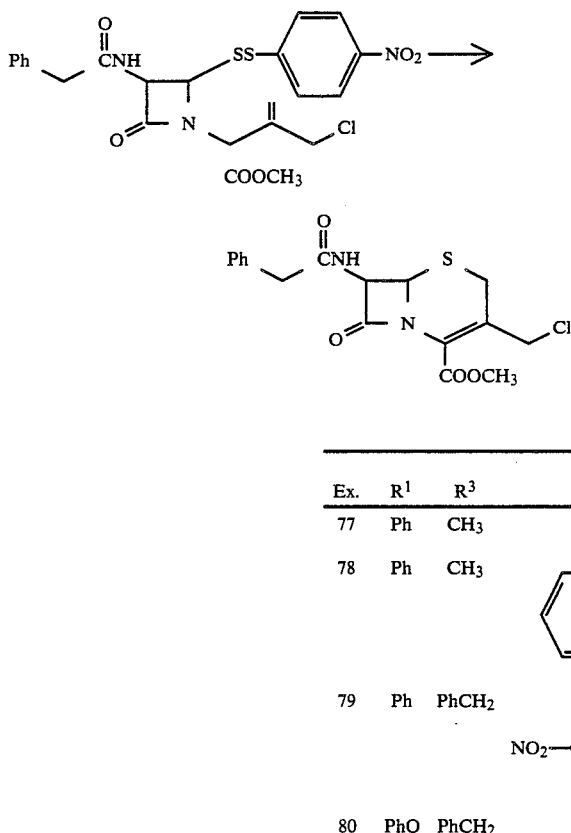

IR (Nujol, cm⁻¹) 1785, 1730, 1680.

NMR (δ, CDCl₃, ppm) 3.38 and 3.60 (ABq, 2H, 18 Hz), 3.60 (s, 2H), 3.83 (s, 3H), 4.40 and 4.57 (ABq, 2H, 12 Hz), 4.95 (d, 1H, 5 Hz), 5.78 (dd, 1H, 5 Hz, 9 Hz), 6.18 (d, 1H, 9 Hz), 7.27 (s, 5H).

EXAMPLES 77 TO 80

The procedure of Example 66 was repeated with the exception of using compounds represented by the formula

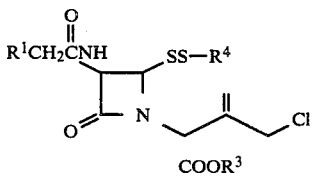

wherein $R^1$, $R^3$ and $R^4$ are as defined in Table 9 below, giving cephem compounds represented by the formula

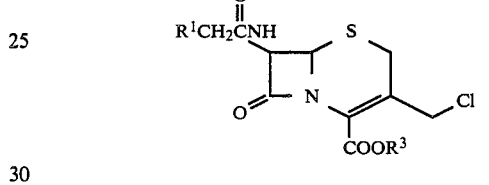

wherein $R^1$ and $R^3$ are as defined in Table 9.

TABLE 9

| Ex. | $R^1$ | $R^3$ | $R^4$ | Solvent | Reactant | Temp. (°C.) | Time (hrs.) | Yield (%) |
|---|---|---|---|---|---|---|---|---|
| 77 | Ph | CH₃ | Ph | DMF | Ammonia water | −25 | 1 | 44 |
| 78 | Ph | CH₃ | 2-pyridyl | DMF | Ammonia water | −25 | 1.33 | 49 |
| 79 | Ph | PhCH₂ | 4-NO₂-C₆H₄ | DMF | Ammonia gas | −30 | 1 | 59 |
| 80 | PhO | PhCH₂ | Ph | DMF | Ammonia gas | −25 | 1 | 45 |

In 0.5 ml of dimethylformamide was dissolved 31 mg of the ester of 2-(3-phenylacetamide-4-(4-nitrophenyldithio)-2-azetidinone-1-yl)-3-chloromethyl-3-butenoic acid and methyl alcohol to obtain a uniform solution. The solution was cooled to −25° C. Thereto was added 58 µl of a solution (about 2 mole) of ammonia gas in dimethylformamide. The resulting mixture was stirred for 1 hour. Thereto were added 5 drops of 5% hydrochloric acid. The mixture was vigorously agitated until it had room temperature. It was diluted with 5 ml of ethyl acetate. The dilute solution was washed with a saturated aqueous solution of sodium chloride, dried over Na₂SO₄ and concentrated. The residue was treated by silica gel column chromatography using a 5:1 benzene-ethyl acetate mixture, giving 14.5 mg of the ester of 7-phenylacetamide-3-chloromethyl-3-cephem-4-carboxylic acid and methyl alcohol. Yield 66%. The compound thus prepared was analyzed with the following results.

The compounds thus prepared, i.e. the ester of 7-phenoxyacetamide-3-chloromethyl-3-cephem-4-carboxylic acid and benzyl alcohol, were analyzed with the following results.

IR (Nujol, cm⁻¹) 1790, 1730, 1690.

NMR (δ, CDCl₃, ppm) 3.50 and 3.55 (ABq, 2H, 18 Hz), 4.40 and 4.53 (ABq, 2H, 12 Hz), 4.52 (s, 2H), 4.97 (d, 1H, 5 Hz), 5.29 (s, 2H), 5.73 (dd, 1H, 5 Hz, 9 Hz), 6.48 (d, 1H, 9 Hz), 7.32 (s, 5H), 6.7–7.6 (m, 5H).

We claim:

1. A process for preparing a thiazolinoazetidinone derivative represented by the formula

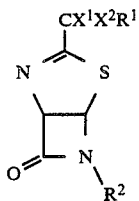
(I)

wherein $X^1$ and $X^2$ each represent a hydrogen atom or halogen atom; $R^1$ represents an aryl selected from the group consisting of phenyl, tolyl, xylyl, naphthyl, p-chlorophenyl, p-methoxyphenyl, p-nitrophenyl and p-hydroxyphenyl or an aryloxy selected from the group consisting of phenoxy, tolyloxy, xylyloxy, naphthyloxy, p-chlorophenyloxy, p-methoxyphenyloxy, p-nitrophenyloxy and p-hydroxyphenyloxy; $R^2$ represents

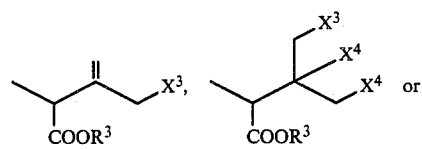

wherein $R^3$ represents a lower alkyl substituted with at least one aryl group selected from the group consisting of benzyl, p-nitrobenzyl, diphenylmethyl, 2-phenylethyl, 2-(p-nitrophenyl)ethyl, 3-phenylpropyl and 3-(p-nitrophenyl)propyl, a lower alkyl substituted with at least one aryloxy group selected from the group consisting of phenoxymethyl, p-nitrophenoxymethyl, 2-phenoxyethyl, 2-(p-nitrophenoxy)ethyl, 3-phenoxypropyl and 3-(p-nitrophenoxy)propyl or a lower alkyl optionally substituted with at least one halogen atom; and $X^3$ and $X^4$, which are the same or different, each represent a halogen atom, and $X^5$ represents $X^3$ and $X^4$, the process comprising electrolyzing a compound of the formula

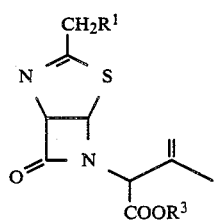

wherein $R^1$ and $R^3$ are as defined above in the presence of halide to produce a thiazolinoazetidinone derivative of the formula

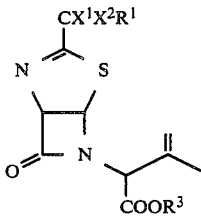
(Ia)

wherein $R^1$, $R^3$, $X^1$ and $X^3$ are as defined above, and optionally permitting halogen under irradiation with light to act on the compound (Ia) to produce a thiazolinoazetidinone derivative of the formula

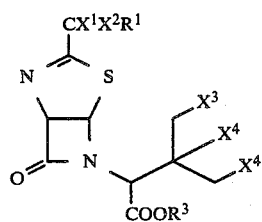
(Ib)

wherein $R^1$, $R^3$, $X^1$, $X^2$, $X^3$ and $X^4$ are as defined above, and optionally bringing a base compound into contact with the compound (Ib) to produce a thiazolinoazetidinone derivative of the formula

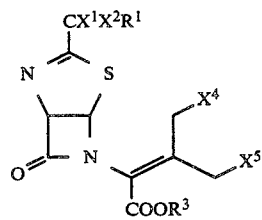
(Ic)

wherein $R^1$, $R^3$, $X^1$, $X^2$, $X^4$ and $R^5$ are as defined above, and optionally permitting zinc to act on a compound

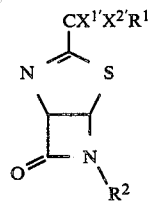

wherein $X^{1'}$ and $X^{2'}$ each represent a halogen atom and $R^1$ and $R^2$ are as defined above in the presence of a lower fatty acid to produce a thiazolinoazetidinone derivative of the formula

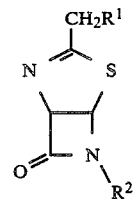

wherein $R^1$ and $R^2$ are as defined above.

2. A process for preparing a thiazolinoazetidinone derivative represented by the formula

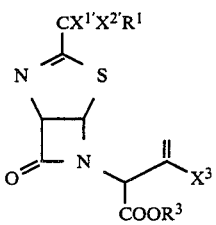

wherein $X^{1'}$ and $X^{2'}$ represent a halogen atom; $R^1$ represents an aryl selected from the group consisting of phenyl, tolyl, xylyl, naphthyl, p-chlorophenyl, p-methoxyphenyl, p-nitrophenyl and p-hydroxyphenyl or an aryloxy selected from the group consisting of phenoxy, tolyloxy, xylyloxy, naphthyloxy, p-chlorophenyloxy, p-methoxyphenyloxy, p-nitrophenyloxy and p-hydroxyphenyloxy; $R^3$ represents a lower alkyl substituted with at least one aryl group selected from the group consisting of benzyl, p-nitrobenzyl, diphenylmethyl, 2-phenylethyl, 2-(p-nitrophenyl)ethyl, 3-phenylpropyl and 3-(p-nitrophenyl)propyl, a lower alkyl substituted with at least one aryloxy group selected from the group consisting of phenoxymethyl, p-nitrophenoxymethyl, 2-phenoxyethyl, 2-(p-nitrophenoxy)ethyl, 3-phenoxypropyl and 3-(p-nitrophenoxy)propyl or a lower alkyl optionally substituted with at least one halogen atom; and $X^3$ represents a halogen atom, the process comprising electrolyzing a compound of the formula

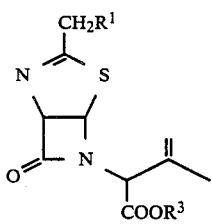

wherein $R^1$ and $R^3$ are as defined above in the presence of halide.

3. A process for preparing a thiazolinoazetidinone derivative represented by the formula

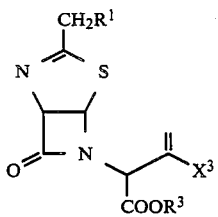

wherein $R^{1'}$ represents an aryl selected from the group consisting of phenyl, tolyl, xylyl, naphthyl, p-chlorophenyl, p-methoxyphenyl, p-nitrophenyl and p-hydroxyphenyl or an aryloxy selected from the group consisting of phenoxy, tolyloxy, xylyloxy, naphthyloxy, p-chlorophenyloxy, p-methoxyphenyloxy, p-nitrophenyloxy and p-hydroxyphenyloxy; $R^3$ represents a lower alkyl substituted with at least one aryl group selected from the group consisting of benzyl, p-nitrobenzyl, diphenylmethyl, 2-phenylethyl, 2-(p-nitrophenyl)ethyl, 3-phenylpropyl and 3-(p-nitrophenyl)propyl, a lower alkyl substituted with at least one aryloxy group selected from the group consisting of phenoxymethyl, p-nitrophenoxymethyl, 2-phenoxyethyl, 2-(p-nitrophenoxy)ethyl, 3-phenoxypropyl and 3-(p-nitrophenoxy)propyl or a lower alkyl optionally substituted with at least one halogen atom; and $X^3$ represents a halogen atom, the process comprising electrolyzing a compound of the formula

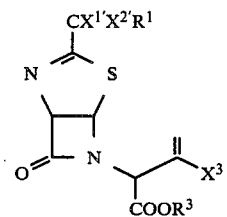

wherein $R^1$, $R^3$ and $X^3$ are as defined above, and $X^{1'}$ and $X^{2'}$ represents a halogen atom in the presence of lower fatty acid.

4. A process for preparing a thiazolinoazetidinone derivative represented by the formula

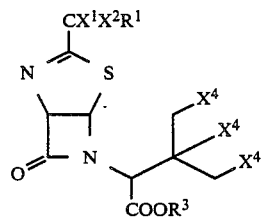

wherein $X^1$ and $X^2$ represent a halogen atom or hydrogen atom; $R^1$ represents an aryl selected from the group consisting of phenyl, tolyl, xylyl, naphthyl, p-chlorophenyl, p-methoxyphenyl, p-nitrophenyl and p-hydroxyphenyl or an aryloxy selected from the group consisting of phenoxy, tolyloxy, xylyloxy, naphthyloxy, p-chlorophenyloxy, p-methoxyphenyloxy, p-nitrophenyloxy and p-hydroxyphenyloxy; $R^3$ represents a lower alkyl substituted with at least one aryl group selected from the group consisting of benzyl, p-nitrobenzyl, diphenylmethyl, 2-phenylethyl, 2-(p-nitrophenyl) ethyl, 3-phenylpropyl and 3-(p-nitrophenyl)propyl, a lower alkyl substituted with at least one aryloxy group selected from the group consisting of phenoxymethyl, p-nitrophenoxymethyl, 2-phenoxyethyl, 2-(p-nitrophenoxy)ethyl, 3-phenoxypropyl and 3-(p-nitrophenoxy)propyl or a lower alkyl optionally substituted with at least one halogen atom; and $X^3$ and $X^4$, which are the same or different, each represent a halogen atom, the process comprising reacting a compound of the formula

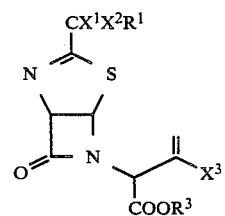

wherein $X^1$, $X^2$, $R^1$, $R^3$ and $X^3$ are as defined above, with a halogen in a suitble organic solvent while irradiating the reaction mixture with light of a tungsten lamp.

5. A process for preparing a thiazolinoazetidinone derivative represented by the formula

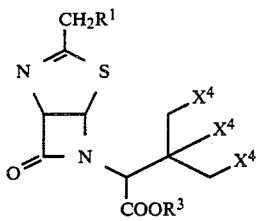

wherein $R^1$ represents an aryl selected from the group consisting of phenyl, tolyl, xylyl, naphthyl, p-chlorophenyl, p-methoxyphenyl, p-nitrophenyl and p-hydroxyphenyl or an aryloxy selected from the group consisting of phenoxy, tolyloxy, xylyloxy, naphthyloxy, p-chlorophenyloxy, p-methoxyphenyloxy, p-nitrophenyloxy and p-hydroxyphenyloxy; $R^3$ represents a lower alkyl substituted with at least one aryl group selected from the group consisting of benzyl, p-nitrobenzyl, diphenylmethyl, 2-phenylethyl, 2-(p-nitrophenyl)ethyl, 3-phenylpropyl and 3-(p-nitrophenyl)propyl, a lower alkyl substituted with at least one aryloxy group selected from the group consisting of phenoxymethyl, p-nitrophenoxymethyl, 2-phenoxyethyl, 2-(p-nitrophenoxy)ethyl, 3-phenoxypropyl and 3-(p-nitrophenoxy)propyl or a lower alkyl optionally substituted with at least one halogen atom; and $X^3$ and $X^4$, which are the same or different, each represent a halogen atom, the process comprising permitting zinc to act on a compound represented by the formula

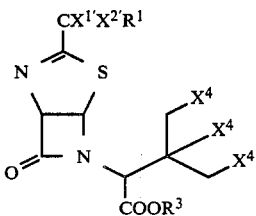

wherein $R^1$, $R^3$ $X^3$ and $X^4$ are as defined above, and $X^{1'}$ and $X^{2'}$ represent a halogen atom in the presence of lower fatty acid.

6. A process for preparing a thiazolinoazetidinone derivative represented by the formula

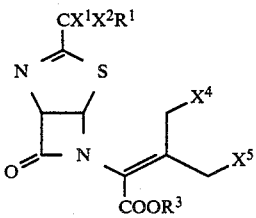

wherein $X^1$ and $X^2$ each represent a hydrogen atom or halogen atom; $R^1$ represents an aryl selected from the group consisting of phenyl, tolyl, xylyl, naphthyl, p-chlorophenyl, p-methoxyphenyl, p-nitrophenyl and p-hydroxyphenyl or an aryloxy selected from the group consisting of phenoxy, tolyloxy, xylyloxy, naphthyloxy, p-chlorophenyloxy, p-methoxyphenyloxy, p-nitrophenyloxy and p-hydroxyphenyloxy; $R^3$ represents a lower alkyl substituted with at least one aryl group selected from the group consisting of benzyl, p-nitrobenzyl, diphenylmethyl, 2-phenylethyl, 2-(p-nitrophenyl)ethyl, 3-phenylpropyl and 3-(p-nitrophenyl)propyl, a lower alkyl substituted with at least one aryloxy group selected from the group consisting of phenoxymethyl, p-nitrophenoxymethyl, 2-phenoxyethyl, 2-(p-nitrophenoxy)ethyl, 3-phenoxypropyl and 3-(p-nitrophenoxy)propyl or a lower alkyl optionally substituted with at least one halogen atom; and $X^4$ and $X^5$, which are the same or different, each represent a halogen atom, the process comprising bringing an organic amine into contact with a compound represented by the formula

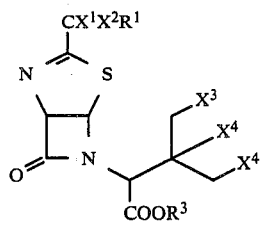

wherein $R^1$, $R^3$, $X^1$, $X^2$ and $X^4$ are as defined above, and $X^3$ represents a halogen atom.

7. A process for preparing a thiazolinoazetidinone derivative represented by the formula

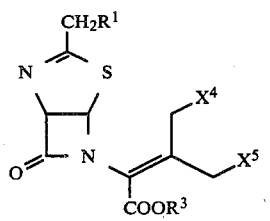

wherein $X^1$ and $X^2$ each represent a hydrogen atom or halogen atom; $R^1$ represents an aryl selected from the group consisting of phenyl, tolyl, xylyl, naphthyl, p-chlorophenyl, p-methoxyphenyl, p-nitrophenyl and p-hydroxyphenyl or an aryloxy selected from the group consisting of phenoxy, tolyloxy, xylyloxy, naphthyloxy, p-chlorophenyloxy, p-methoxyphenyloxy, p-nitrophenyloxy and p-hydroxyphenyloxy; $R^3$ represents a lower alkyl substituted with at least one aryl group selected from the group consisting of benzyl, p-nitrobenzyl, diphenylmethyl, 2-phenylethyl, 2-(p-nitrophenyl)ethyl, 3-phenylpropyl and 3-(p-nitrophenyl)propyl, a lower alkyl substituted with at least one aryloxy group selected from the group consisting of phenoxymethyl, p-nitrophenoxymethyl, 2-phenoxyethyl, 2-(p-nitrophenoxy)ethyl, 3-phenoxypropyl and 3-(p-nitrophenoxy)propyl or a lower alkyl optionally substituted with at least one halogen atom; and $X^4$ and $X^5$, which are the same or different, each represent a halogen atom, the process comprising permitting zinc to act on a compound represented by the formula

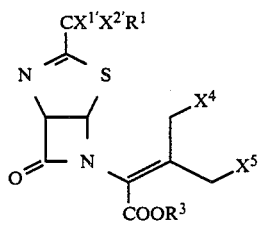

wherein $R^1$, $R^3$, $X^4$ and $X^5$ are as defined above, and $X^{1'}$ and $X^{2'}$ represent a halogn atom in the presence of lower fatty acid.

8. A process as defined in claim 2 in which the halide is used in an amount of about 0.5 to about 10 moles per mole of the starting compound.

9. A process as defined in claim 2 in which the electrolysis is conducted in the presence of hydrohalogenic acid.

10. A process as defined in claim 9 in which the hydrohalogenic acid is hydrochloric acid.

11. A process as defined in claim 2 in which the halide is chloride.

12. A process as defined in claim 2 in which a mineral acid or organic acid is present in the reaction system.

13. A process as defined in claim 12 in which the mineral acid is at least one acid selected from the group consisting of sulfuric acid, sodium hydrogensulfate, potassium hydrogensulfate, phosphoric acid and boric acid.

14. A process as defined in claim 12 in which the organic acid is at least one species selected from the group consisting of formic acid, acetic acid, propionic acid, butyric acid, oxalic acid, citric acid, p-toluenesulfonic acid and methanesulfonic acid.

15. A process as defined in any one of claims 12 to 14 in which the mineral acid or organic acid is present in the reaction system in an amount of about 0.5 to about 10 moles per mole of the starting compound.

16. A process as defined in any one of claims 2, 8-10, 11-14 in which the electrolysis is carried out at a cathode current density of about 1 to about 500 mA/cm².

17. A process as defined in any one of claims 2, 8-10, and 11-14 in which the electrolysis is conducted at a temperature of about −30° to about 60° C.

18. A process as defined in claim 3 in which the lower fatty acid is present in the reaction system in an amount of about 1 to about 10 moles per mole of the starting compound.

19. A process as defined in claim 3 in which the zinc is used in an amount of about 1 to about 10 moles per mole of the starting compound.

20. A process as defined in any one of claims 3, 18, 19 in which the reaction is carried out at a temperature of about −50° to about 30° C.

21. A process as defined in claim 4 in which the halogen is used in an amount of about 0.5 to about 10 moles per mole of the starting compound.

22. A process as defined in claim 4 in which the organic solvent is at least one species selected from the group consisting of dichloromethane, dichloroethane, chloroform, carbon tetrachloride, methyl acetate, ethyl acetate, methyl formate, butyl acetate, ethyl propionate, diethyl ether, dibutyl ether, tetrahydrofuran, dioxane, acetonitrile, butyronitrile, pentane, hexane, cyclohexane, benzene, toluene, xylene, chlorobenzene and carbon disulfide.

23. A process as defined in claim 4 in which the reaction is carried out at a temperature of about −20° to about 100° C.

24. A process as defined in claim 5 in which the lower fatty acid is present in the reaction system in an amount of about 1 to about 10 moles per mole of the starting compound.

25. A process as defined in claim 5 in which the zinc is used in an amount of about 1 to about 10 moles per mole of the starting compound.

26. A process as defined in claim 5 in which the reaction is carried out at a temperature of about −50° to about 30° C.

27. A process as defined in claim 6 in which the base is used in an amount of about 0.5 to about 10 moles per mole of the starting compound.

28. A process as defined in claim 6 in which the base is an organic amine.

29. A process as defined in claim 28 in which the organic amine is at least species selected from the group consisting of dimethylamine, diethylamine, triethylamine, ethyldiisopropylamine, piperidine, lutidine, pyridine, 1,5-diazabicyclo[5,4,0]undecene-5 and 1,5-diazabicyclo[4,3,0]nonene-5.

30. A process as defined in claim 6 in which the reaction is carried out at a temperature of about −20° to about 80° C.

31. A process as defined in claim 7 in which the lower fatty acid is present in the reaction system in an amount of about 1 to about 10 moles per mole of the starting compound.

32. A process as defined in claim 7 in which the zinc is used in an amount of about 1 to about 10 moles per mole of the starting compound.

33. A process as defined in any one of claims 7, 31, 32 in which the reaction is carried out at a temperature of about −50° to about 30° C.

* * * * *